(12) United States Patent
Cronenberg et al.

(10) Patent No.: US 9,522,239 B2
(45) Date of Patent: Dec. 20, 2016

(54) MEDICAL INJECTOR WITH RATCHETING PLUNGER

(71) Applicant: Becton, Dickinson and Company, Franklin Lakes, NJ (US)

(72) Inventors: Richard Cronenberg, Mahwah, NJ (US); Haiming Wu, Weston, MA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 336 days.

(21) Appl. No.: 14/329,753

(22) Filed: Jul. 11, 2014

(65) Prior Publication Data

US 2014/0323980 A1 Oct. 30, 2014

Related U.S. Application Data

(60) Division of application No. 13/064,315, filed on Mar. 17, 2011, now Pat. No. 8,920,384, which is a
(Continued)

(51) Int. Cl.
*A61M 5/315* (2006.01)
*A61M 5/31* (2006.01)

(52) U.S. Cl.
CPC ....... *A61M 5/31555* (2013.01); *A61M 5/3158* (2013.01); *A61M 5/31581* (2013.01);
(Continued)

(58) Field of Classification Search
CPC .. A61M 5/24; A61M 5/3158; A61M 5/31593; A61M 5/31555; A61M 5/31581; A61M 5/31585; A61M 5/31551; A61M 5/31578; A61M 2005/31508; A61M 5/3155
See application file for complete search history.

(56) References Cited

U.S. PATENT DOCUMENTS 3,517,668 A 6/1970 Brickson
4,364,388 A 12/1982 Cech
(Continued)

FOREIGN PATENT DOCUMENTS

EP 0272035 A2 6/1988
EP 1923083 A1 5/2008
(Continued)

*Primary Examiner* — Kevin C Sirmons
*Assistant Examiner* — William Carpenter
(74) *Attorney, Agent, or Firm* — Dickinson Wright PLLC

(57) ABSTRACT

A medical injector has a body with a displaceable plunger. The plunger includes a plurality of spaced-apart ratchet teeth disposed along the length thereof. At least one indexer is provided to engage the plunger, wherein the indexer is configured to allow the plunger to displace distally toward a distal end of the body but not proximally toward a proximal end of the body. The medical injector also includes an actuator having an engagement portion formed to engage one or more of the ratchet teeth. The actuator is displaceable to a ready state, the engagement portion being displaced proximally relative to the plunger with the actuator being displaced to the ready state. The indexer prevents proximal movement of the plunger, thereby allowing the engagement portion to bypass one or more of the ratchet teeth with the actuator being displaced to the ready state. In addition, the actuator is displaceable from the ready state to cause actuation of the medical injector. The displacement from the ready state causes distal displacement of the engagement portion with the engagement portion engaging one or more of the ratchet teeth and causing distal displacement of the plunger with the engagement portion.

10 Claims, 25 Drawing Sheets

Related U.S. Application Data continuation-in-part of application No. PCT/US2009/057429, filed on Sep. 18, 2009.

(60) Provisional application No. 61/192,468, filed on Sep. 18, 2008.

(52) U.S. Cl.
CPC ............... *A61M 2005/3125* (2013.01); *A61M 2005/3126* (2013.01)

(56) References Cited

U.S. PATENT DOCUMENTS

| | | | |
|---|---|---|---|
| 4,820,287 A | 4/1989 | Leonard | |
| 4,865,591 A | 9/1989 | Sams | |
| 4,973,318 A | 11/1990 | Holm et al. | |
| 5,224,936 A | 7/1993 | Gallagher | |
| 5,433,352 A | 7/1995 | Ronvig | |
| 5,496,293 A | 3/1996 | Huggenberger | |
| 5,611,783 A | 3/1997 | Mikkelsen | |
| 5,643,214 A | 7/1997 | Marshall et al. | |
| 5,755,362 A | 5/1998 | Rodriguez et al. | |
| 5,807,346 A | 9/1998 | Frezza | |
| 6,004,297 A | 12/1999 | Steenfeldt-Jensen et al. | |
| 6,235,004 B1 * | 5/2001 | Steenfeldt-Jensen | A61M 5/31551 604/207 |
| 6,439,439 B1 | 8/2002 | Rickard et al. | |
| 6,562,006 B1 * | 5/2003 | Hjertman | A61M 5/31553 604/208 |
| 6,672,489 B1 | 1/2004 | Huang | |
| 6,689,101 B2 | 2/2004 | Hjertman et al. | |
| 6,699,224 B2 | 3/2004 | Kirchhofer et al. | |
| 6,793,646 B1 | 9/2004 | Giambattista et al. | |
| 7,025,757 B2 | 4/2006 | Reilly et al. | |
| 7,297,136 B2 | 11/2007 | Wyrick | |
| 7,390,319 B2 | 6/2008 | Friedman | |
| 7,678,084 B2 | 3/2010 | Judson et al. | |
| 7,749,200 B2 | 7/2010 | Graf et al. | |
| 7,771,399 B2 | 8/2010 | Burren et al. | |
| 7,854,726 B2 | 12/2010 | Fago et al. | |
| 7,867,197 B2 | 1/2011 | Sims et al. | |
| 7,867,202 B2 | 1/2011 | Moser et al. | |
| 7,993,301 B2 | 8/2011 | Boyd et al. | |
| 8,038,655 B2 | 10/2011 | Burren et al. | |
| 8,070,713 B2 | 12/2011 | Matusch | |
| 8,267,900 B2 | 9/2012 | Harms et al. | |
| 8,540,683 B2 | 9/2013 | Williams et al. | |
| 8,672,899 B2 | 3/2014 | Diller et al. | |
| 2001/0051792 A1 | 12/2001 | Kirchhofer et al. | |
| 2002/0007142 A1 | 1/2002 | Hjertman et al. | |
| 2002/0165500 A1 | 11/2002 | Bechtold et al. | |
| 2004/0127858 A1 * | 7/2004 | Bendek | A61M 5/31541 604/208 |
| 2007/0043319 A1 | 2/2007 | Kimmel et al. | |
| 2007/0233004 A1 | 10/2007 | Sims et al. | |
| 2008/0071227 A1 | 3/2008 | Moser et al. | |
| 2008/0077094 A1 | 3/2008 | Burren et al. | |
| 2010/0094206 A1 | 4/2010 | Boyd et al. | |
| 2010/0105003 A1 | 4/2010 | Weill et al. | |
| 2011/0034870 A1 | 2/2011 | Glejboel et al. | |

FOREIGN PATENT DOCUMENTS

| | | |
|---|---|---|
| FR | 2913341 A1 | 9/2008 |
| JP | 358-168334 | 5/1982 |
| JP | U-S61-008055 | 1/1986 |
| JP | U-H05-062255 | 8/1993 |
| JP | H07-501249 A | 2/1995 |
| JP | H09-503150 A | 3/1997 |
| JP | 2003-525667 A | 9/2003 |
| JP | 2006204918 A | 8/2006 |
| JP | 2007534345 A | 11/2007 |
| JP | 2008119075 A | 5/2008 |
| JP | 2010509958 A | 4/2010 |
| WO | WO-9406494 A1 | 3/1994 |
| WO | WO-9413339 A1 | 6/1994 |
| WO | 9607443 A1 | 3/1996 |
| WO | WO02070049 A1 | 9/2002 |
| WO | WO-03020347 A2 | 3/2003 |
| WO | WO2006079900 A2 | 8/2006 |
| WO | WO2008058668 A1 | 5/2008 |
| WO | 2009121194 A1 | 10/2009 |
| WO | 2010/033770 A2 | 3/2010 |
| WO | WO-2011039215 A1 | 4/2011 |

\* cited by examiner

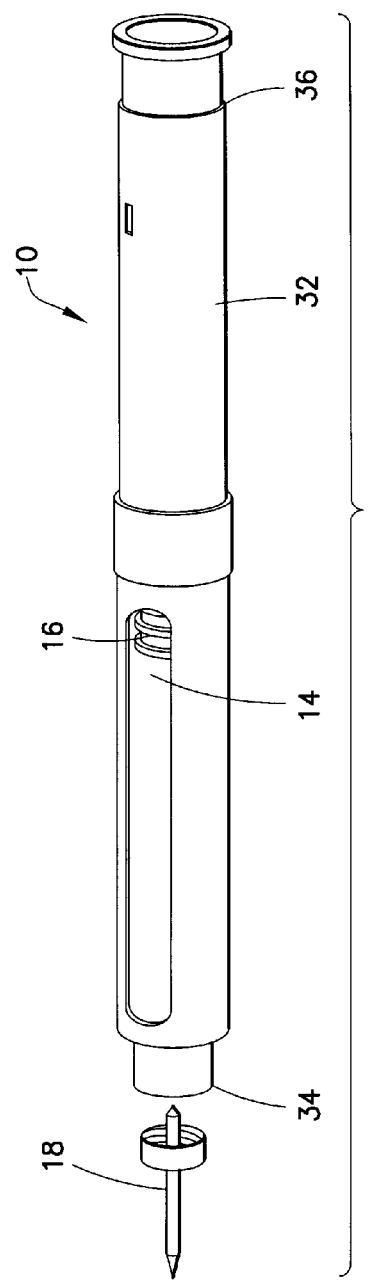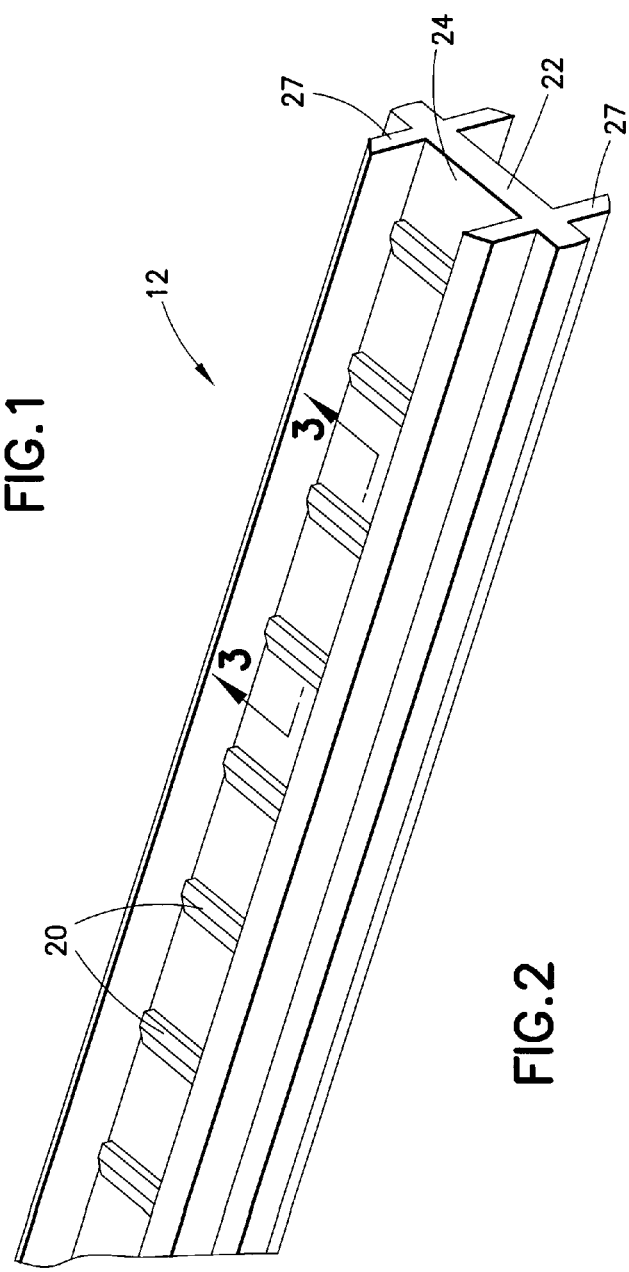

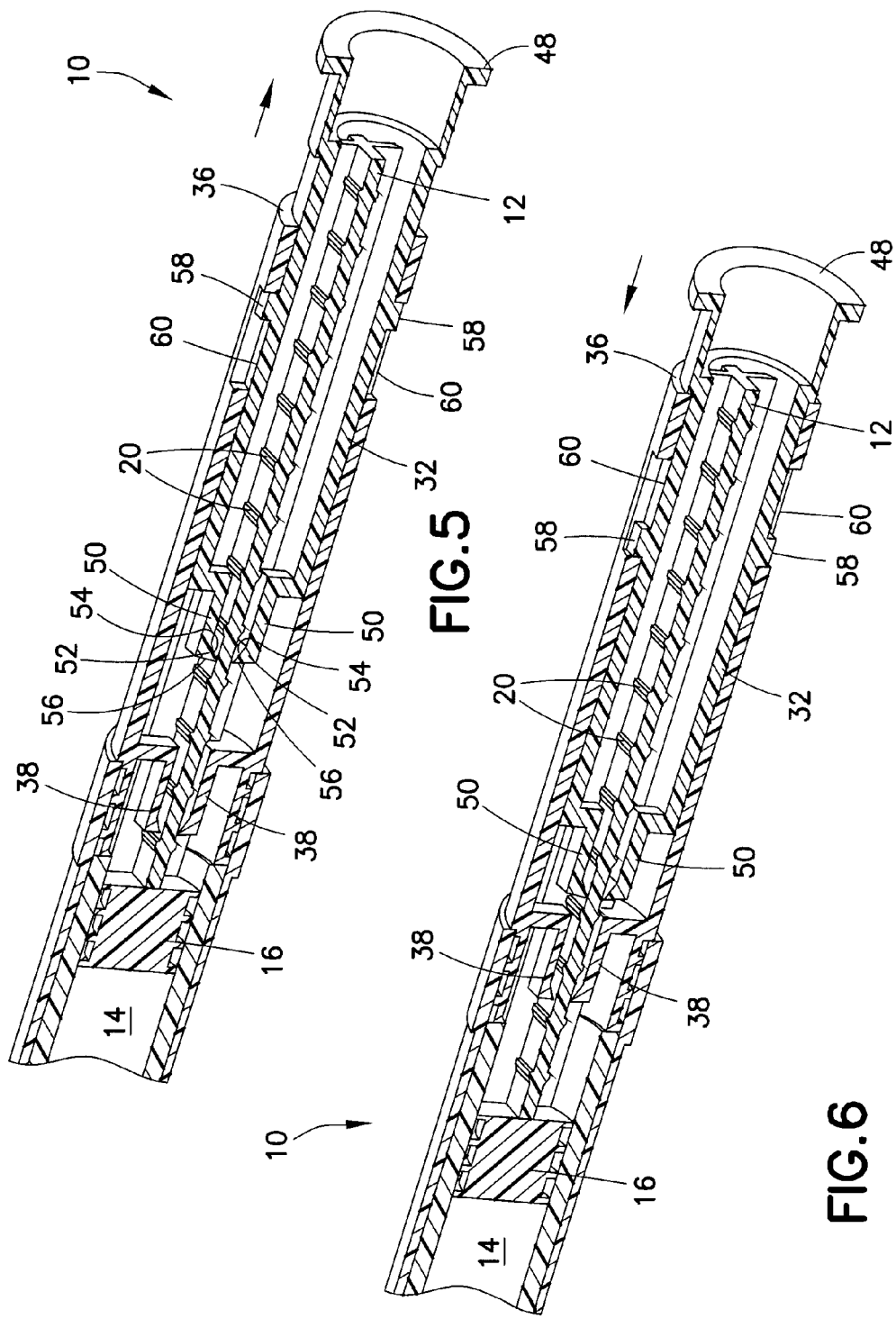

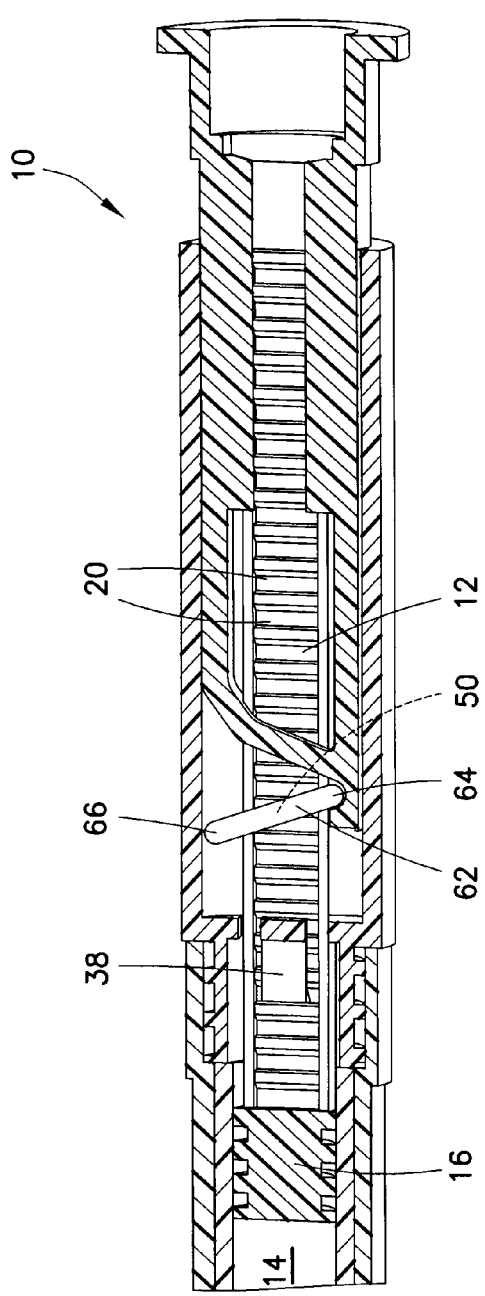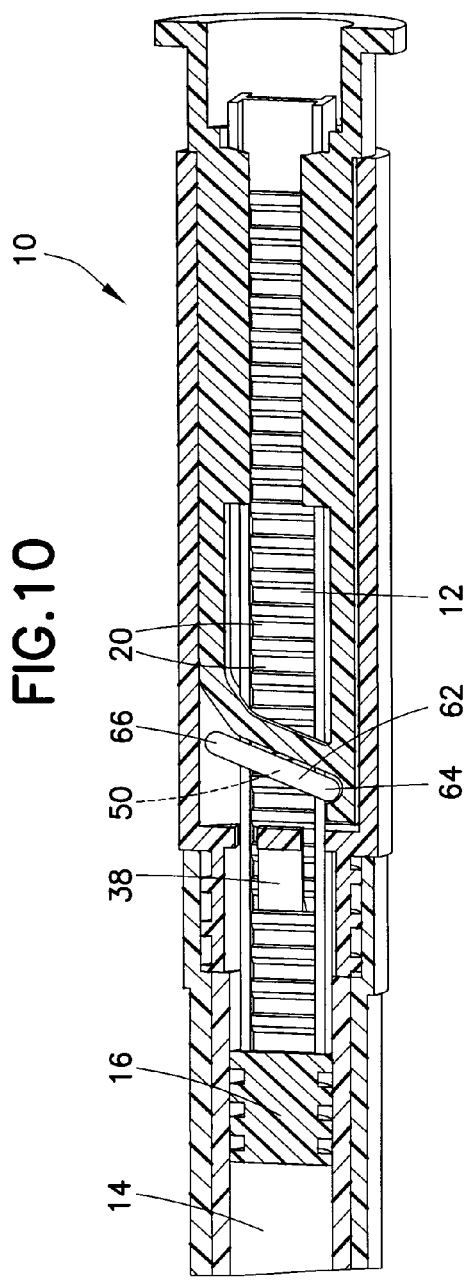

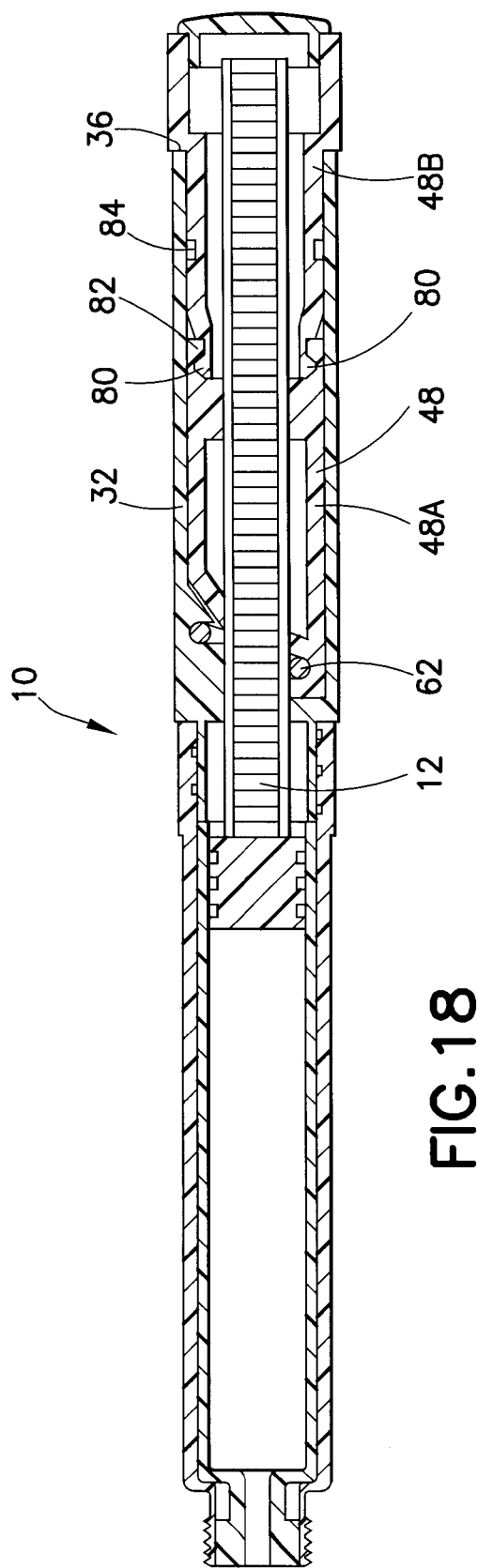
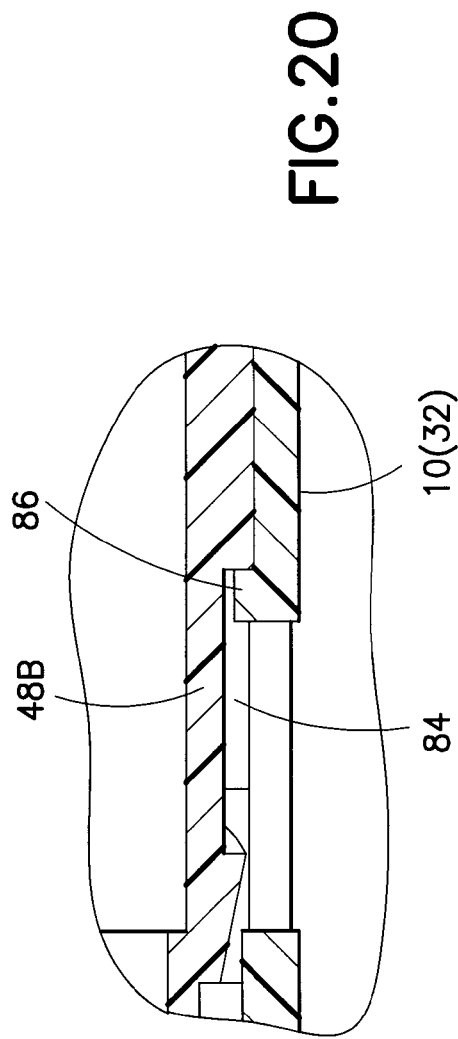
FIG. 18
FIG. 20

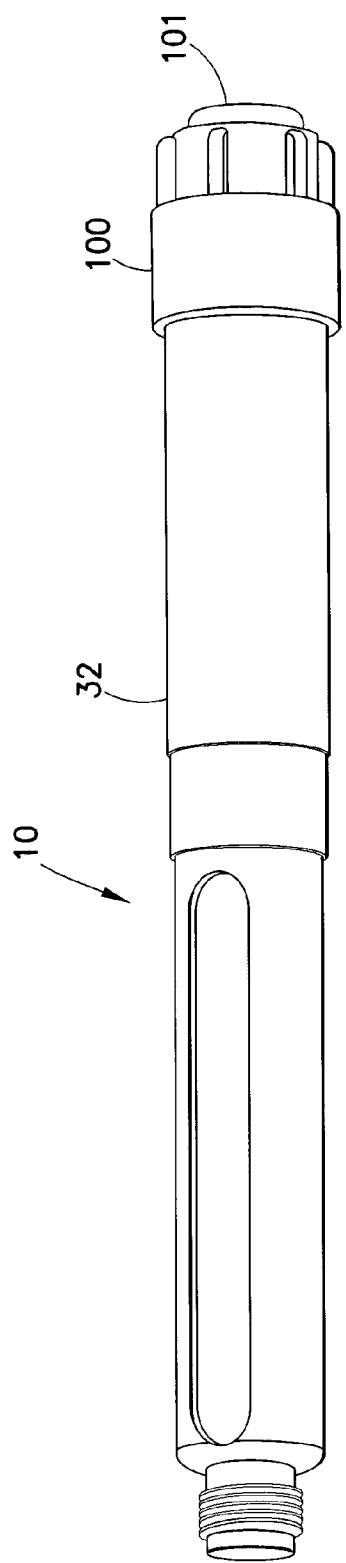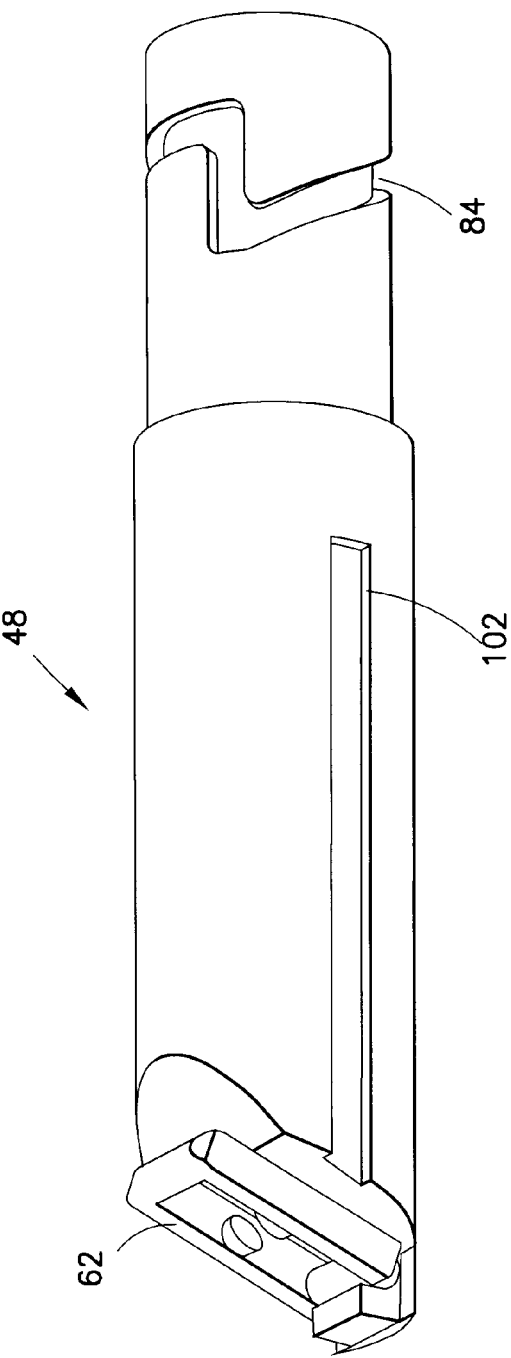

MEDICAL INJECTOR WITH RATCHETING PLUNGER

CROSS-REFERENCE TO RELATED APPLICATION

This application is a division of U.S. patent application Ser. No. 13/064,315 filed Mar. 17, 2011, which is a continuation-in-part of International Patent Application No. PCT/US2009/057429, filed in English on Sep. 18, 2009 and designating the United States. International Patent Application No. PCT/US2009/057429 claims priority under 35 USC §119(e) from U.S. Provisional Patent Application Ser. No. 61/192,468, filed on Sep. 18, 2008. The entirety of all of said prior applications is hereby incorporated by reference.

FIELD OF THE INVENTION

This invention relates to displaceable medical injector plungers and, more particularly, to ratcheting medical injector plungers.

BACKGROUND OF THE INVENTION

Medical injectors are well known in the art, including syringes and pen injectors. Medical injectors typically include a plunger for advancing one or more stoppers in delivering a medicament during an injection. Although it is known in the prior art to provide syringe plungers with teeth or other features to prevent retraction and re-use after an initial injection, syringe plungers are typically actuated through direct application of linear force. Dose size is a direct function of plunger displacement. It may be difficult to control linear displacement of the plunger, thus resulting in difficulty over control of dose size.

As for pen injectors, a lead screw or rotating plunger is provided which is mechanically coupled to a dose-setting knob or other actuator through a series of mechanical connections. The typical pen injector mechanism is fairly complex and consists of multiple cooperating parts. For costs reasons and simplicity of use, a minimum number of working parts is desired.

SUMMARY OF EMBODIMENTS OF THE INVENTION

Accordingly, it is an aspect of the present invention to provide a plunger for a medical injector which may be controllably advanced with a minimum number of cooperating parts.

The foregoing and/or other aspects of the present invention are achieved by providing a medical injector including a body having a distal end and a proximal end, and a displaceable plunger disposed in the body. The plunger includes a plurality of spaced-apart ratchet teeth disposed along the length thereof. At least one indexer is provided and is formed to engage the plunger, wherein the indexer is configured to allow the plunger to displace distally toward a distal end of the body but not proximally toward a proximal end of the body. The medical injector also includes an actuator having an engagement portion formed to engage one or more of the ratchet teeth. The actuator is displaceable to a ready state, the engagement portion being displaced proximally relative to the plunger with the actuator being displaced to the ready state. The indexer prevents proximal movement of the plunger thereby allowing the engagement portion to bypass one or more of the ratchet teeth with the actuator being displaced to the ready state. In addition, the actuator is displaceable from the ready state to cause actuation of the medical injector. The displacement from the ready state causes distal displacement of the engagement portion with the engagement portion engaging one or more of the ratchet teeth and causing distal displacement of the plunger with the engagement portion.

The foregoing and/or other aspects of the present invention are also achieved by providing a medical injector including a body having a distal end and a proximal end, and a plunger displaceably disposed in the body. The plunger includes a plurality of spaced-apart ratchet teeth disposed along the length thereof. The plunger selectively displaces a stopper to dispense a medicament from said medical injector. The medical injector also includes an indexer disposed within the body to engage the plunger to permit distal displacement of the plunger and substantially prevent proximal displacement of the plunger, and an actuator having an engagement portion to engage the plunger to permit proximal displacement of the actuator relative to the plunger and substantially prevent distal displacement of the actuator relative to the plunger. Upon proximal displacement of the actuator relative to the body to a ready state, one or more of the ratchet teeth bypass the engagement portion to proximally displace the actuator relative to the plunger. Upon distal displacement of the actuator relative to the body from the ready state, the actuator engages one or more of the ratchet teeth to distally displace the plunger relative to the indexer to distally displace the stopper to dispense medicament from the medical injector.

The foregoing and/or other aspects of the present invention are also achieved by providing a medical injector including a body having a distal end and a proximal end, and a plunger displaceably disposed in the body. The plunger includes a plurality of spaced-apart ratchet teeth disposed along the length thereof. The plunger selectively displaces a stopper to dispense a medicament from said medical injector. The medical injector also includes an indexer disposed within the body to engage the plunger to permit distal displacement of the plunger and substantially prevent proximal displacement of the plunger. The medical injector additionally includes actuating means for actuating the medical device, the actuating means having engagement means for engaging the plunger to permit proximal displacement of the actuating means relative to the plunger and substantially prevent distal displacement of the actuating means relative to the plunger. Upon proximal displacement of the actuating means relative to the body to a ready state, one or more of the ratchet teeth bypass the engagement means to proximally displace the actuating means relative to the plunger. Upon distal displacement of the actuating means relative to the body from the ready state, the actuating means engages one or more of the ratchet teeth to distally displace the plunger relative to the indexer to distally displace the stopper to dispense medicament from the medical injector.

The foregoing and/or other aspects of the present invention are also achieved by providing a method of injecting a medicament from a medical injector having a body with distal and proximate ends. The method includes the operations of permitting distal displacement of a plunger with respect to the body and substantially preventing proximal displacement of the plunger with respect to the body, and permitting proximal displacement of an actuator relative to the plunger and substantially preventing distal displacement of the actuator relative to the plunger. The method also includes the operations of proximally displacing the actuator relative to the body to a ready state, thereby proximally displacing the actuator relative to the plunger, and distally displacing the actuator relative to the body from the ready state, thereby engaging the plunger and distally displacing the plunger relative to the body to dispense medicament from the medical injector.

Additional and/or other aspects and advantages of the present invention will be set forth in part in the description that follows and, in part, will be apparent from the description, or may be learned by practice of the invention.

BRIEF DESCRIPTION OF THE DRAWINGS

The above and/or other aspects and advantages of embodiments of the invention will become apparent and more readily appreciated from the following detailed description, taken in conjunction with the accompanying drawings, in which FIG. 1 is a perspective view of a medical injector in accordance with an embodiment of present the invention;

FIG. 2 is partial perspective view of a plunger usable with the injector of FIG. 1;

FIGS. 4-6 are perspective partial cross-sectional views illustrating operation of the medical injector of FIG. 1;

FIGS. 9-11 are perspective partial cross-sectional views illustrating operation of a medical injector in accordance with an embodiment of the present invention using the rocker of FIG. 7;

FIG. 18 is a cross-sectional view of a medical injector in accordance with another embodiment of the present invention;

FIG. 20 is a partial cross-sectional view of the medical injector of FIG. 18;

FIG. 28 is a perspective view of the medical injector in accordance with another embodiment of the present invention;

FIG. 29 is a perspective view of an embodiment of an actuator and a rocker of the medical injector of FIG. 28;

DETAILED DESCRIPTION OF EMBODIMENTS OF THE INVENTION

Figure 3:
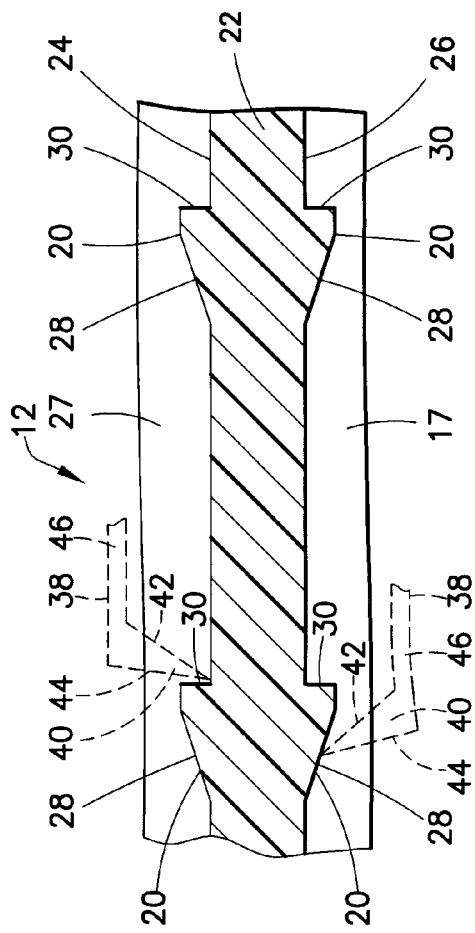
FIG. 3 is a partial cross-sectional view taken along line 3-3 of FIG. 2.

Reference will now be made in detail to embodiments of the present invention, examples of which are illustrated in the accompanying drawings, wherein like reference numerals refer to the like elements throughout. The embodiments described herein exemplify, but do not limit, the present invention by referring to the drawings. As will be understood by one skilled in the art, terms such as up, down, bottom, and top are relative, and are employed to aid illustration, but are not limiting.

With reference to the figures, a medical injector 10 is shown having a ratchetable plunger 12 provided therewith. As will be appreciated by those skilled in the art, the medical injector 10 may be of various forms, including being a syringe or pen injector. In accordance with an embodiment of the present invention, the medical injector 10 is particularly well-suited for administering at least one fixed dose, and is even better suited for administering a series of fixed doses. The medical injector 10 may be configured in any way known to be compatible with the plunger 12 as described herein. The medical injector 10 may include a reservoir 14 for accommodating an injectable medicament, which may be a drug cartridge, or which may be formed directly in the medical injector 10. The reservoir 14 may have one or more stoppers 16 associated therewith as known in the art. The medical injector 10 may also be provided with a needle 18 for injection which may be removably attached or affixed to the medical injector 10 such as in a "staked" arrangement.

The plunger 12 is elongated and generally flat. A plurality of spaced-apart ratchet teeth 20 are disposed along the length of the plunger 12. In a preferred arrangement, the plunger 12 includes a plate-shaped body 22 having opposing first and second faces 24, 26. The ratchet teeth 20 are disposed on the first face 24 and, in a further preferred arrangement, also on the second face 26. Preferably, the ratchet teeth 20 on the first and second faces 24, 26 are axially aligned along the length of the plunger 12.

The ratchet teeth 20 are configured to permit unidirectional movement of the plunger 12. Particularly, with reference to FIG. 3, the ratchet teeth 20 are preferably saw-tooth shaped having a ramped surface 28 and a shoulder stop 30. As shown in FIG. 3, the ramped surfaces 28 of the ratchet teeth 20 on both the first and second surfaces 24, 26 are oriented to face in the same general direction. The shoulder stops 30 extend transversely from the first and second faces 24, 26, preferably at a substantially perpendicular orientation.

The plunger 12 may also have one or more rails 27 extending from the first face 24 and/or the second face 26. The rails 27 may be formed to slide through one or more corresponding shape-mating slots formed in the medical injector 10. The rails 27 may provide stability during use, particularly during translation of the plunger 12.

Figure 4:
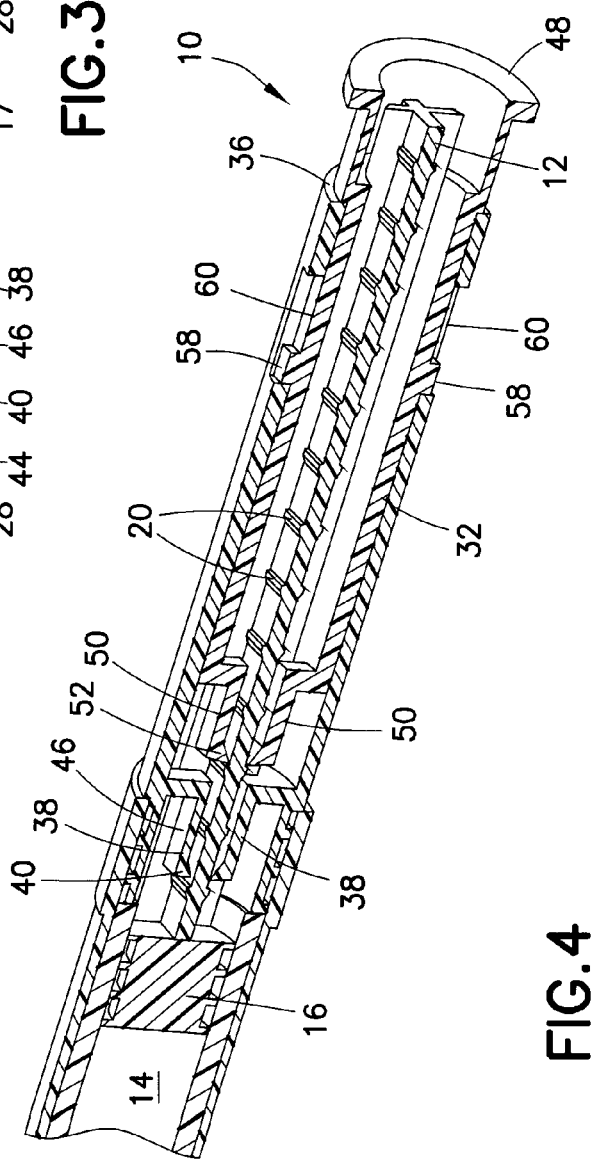

With reference to FIGS. 4-6, the plunger 12 is disposed in a body 32 of the medical injector 10. The body 32 includes a distal end 34, located to be directed toward a patient during an injection, and a proximal end 36, located to be away from a patient during an injection (FIG. 1). During use, the medical injector 10 is configured to permit the plunger 12 to move unidirectionally therein in a distal direction toward the distal end 34, but not in a proximal direction toward the proximal end 36. To facilitate such unidirectional movement, at least one indexer 38 is provided formed to engage the plunger 12. The indexer 38 is configured to allow the plunger 12 to displace distally toward the distal end 34 of the body 32 but not proximally toward the proximal end 36 of the body 32.

The indexer 38 includes a deflectable pawl 40 which, as shown schematically in FIG. 3, includes a ramped engagement surface 42 and an outward facing stop surface 44. The indexer 38 is outwardly deflectable to permit the engagement surface 42 to ascend the ramped surface 28 of an individual of the ratchet teeth 20 with the plunger 12 moving distally relative thereto. With sufficient distal movement, the indexer 38 bypasses the ratchet teeth 12, and under inherent resilience of the indexer 38, snaps inwardly such that the stop surface 44 is aligned with the shoulder stop 30. Preferably, the stop surface 44 is formed to be generally parallel to the shoulder stop 30. With rearward (proximal) movement of the plunger 12, the shoulder stop 30 and the stop surface 44 interferingly engage thus preventing proximal movement of the plunger 12. In a preferred embodiment, a pair of the indexers 38 are provided so as to act against the ratchet teeth 20 located on both the first and second faces 24, 26, as shown in FIGS. 4-6. It is further preferred that a pair of the indexers 38 be provided which are axially aligned thus providing a pinching effect to the plunger 12. This pinching effect may provide a stable holding force for the plunger 12.

The indexer 38 may be formed to be deflectable through inherent resilience, such as through material selection (e.g., being formed of a thermoplastic). In addition, or alternatively, the indexer 38 may include a cantilevered arm 46 which permits deflection of the associated pawl 40. The indexer 38 is formed to have a natural, unbiased state as shown in FIGS. 4-6, where the indexer 38 is positioned to act against the shoulder stop 30 of the ratchet teeth 20. The cantilevered arm 46 is formed with sufficient internal memory to provide the unbiased state for the indexer 38.

The medical injector 10 also includes an actuator 48 having an engagement portion 50 formed to engage one or more of the ratchet teeth 20. The engagement portion 50 preferably includes an engagement pawl 52 having a ramped engagement surface 54 and an outward facing stop surface 56 configured like the pawl 40 described above. Preferably, two of the engagement portions 50 are provided located to engage the ratchet teeth 20 located on the first and second faces 24, 26.

With reference to FIG. 4, the plunger 12 is positioned to engage one of the stoppers 16. To cause actuation of the medical injector 10, as shown in FIG. 5, the actuator 48 is moved to a ready state, with the engagement portion 50 moving proximally. The indexer 38 prevents proximal movement of the plunger 12, thus allowing the actuator 48 to move proximally relative to the plunger 12. With the plunger 12 being held stationary, and the engagement portion 50 moving proximally relative to the plunger 12, the engagement portion 50 bypasses one or more of the ratchet teeth 20. The actuator 48 is displaced sufficiently to achieve a ready state.

For actuation of the medical injector 10, the actuator 48 is displaced from the ready state with distal movement of the engagement portion 50. The engagement portion 50 engages one or more of the ratchet teeth 20, particularly with interfering engagement between the shoulder stop 30 and the stop surface 56. In particular, the engagement portion 50 engages the next distal ratchet tooth 20. Distal movement of the engagement portion 50 causes the plunger 12 to move distally therewith. Distal movement of the plunger 12, in turn, causes distal advancement of the stopper 16 in causing an injection to be administered. The ratchet teeth 20 are able to bypass the indexer 38 in the distal direction.

The size of a dose to be administered by the medical injector 10 is a function of the spacing between the ratchet teeth 20 and/or the amount of proximal displacement of the engagement portion 50 relative to the ratchet teeth 20 with the actuator 48 moving to a ready state. To create a fixed dose, one or more keys 58 may be defined on the medical injector 10 and/or the actuator 48 which are formed to nest within and slide along corresponding channels 60 formed in the medical injector 10 and/or the actuator 48. As shown in FIGS. 4-6, it is preferred that the keys 58 be formed on the actuator 48 and the channels 60 be formed in the medical injector 10. With reference to FIG. 4, the keys 58 are at the distal end of the channel 60, prior to use. With proximal displacement of the actuator 48, the keys 58 are proximally advanced in the channels 60 to a proximal-most position corresponding to the ready state of the actuator 48. The length of the travel of the keys 58 in the channels 60 restricts the range of movement of the actuator 48 in defining the size of the dose administrable by the medical injector 10. As shown in FIGS. 5 and 6, the keys 58 are advanced distally with the actuator 48 during use to a distal-most position.

Figure 7:
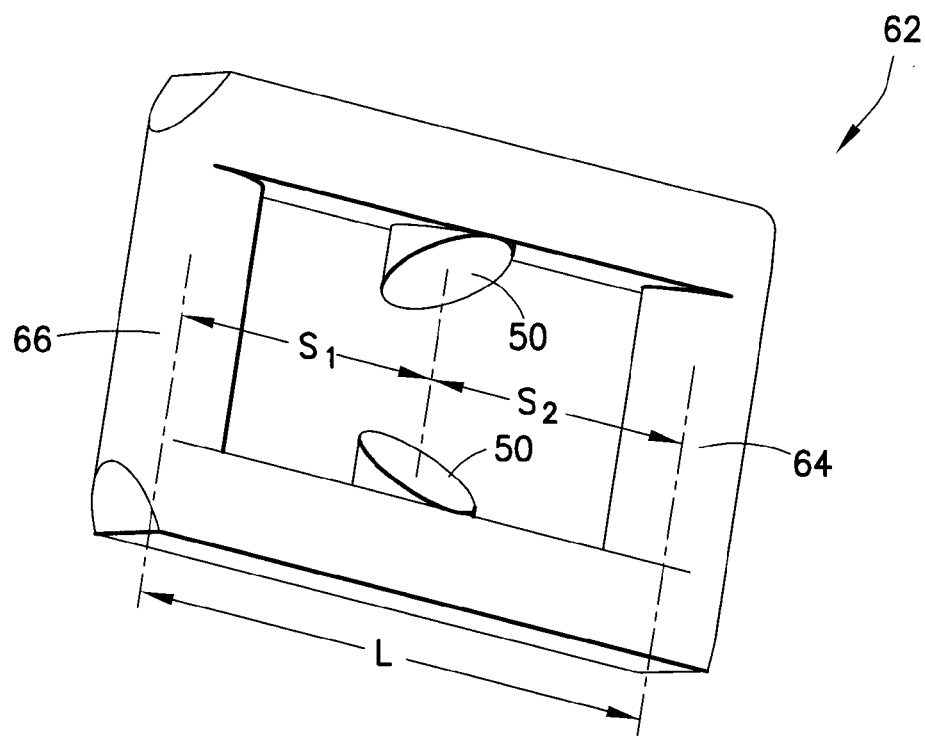
FIGS. 7 and 8 are perspective views respectively illustrating two rockers usable with the injector of FIG. 1.
Figure 8:
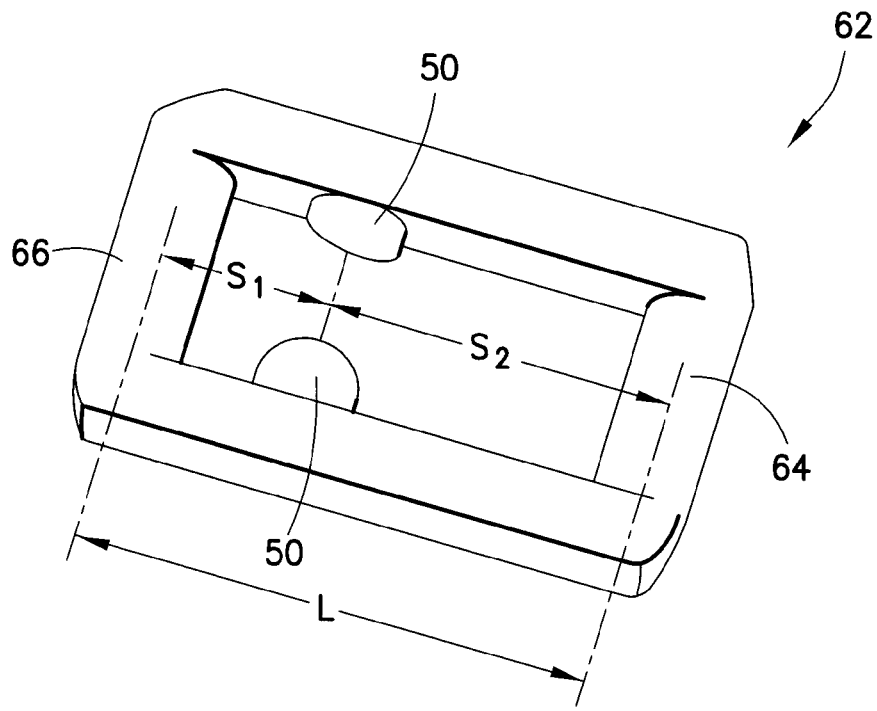

The actuator 48 shown in FIGS. 4-6 is a linear slide actuator which applies force directly to the plunger 12. As will be appreciated by those skilled in the art, the actuator 48 may be of various configurations. With reference to FIGS. 7-8, the actuator 48 may include a rocker 62 pivotally mounted thereto. The rocker 62 is frame-shaped, having a first end 64 for pivotal mounting to the actuator 48 and a second opposing end 66 for pivotally mounting to the medical injector 10. The engagement portion 50 is located between the first and second ends 64, 66. As shown in FIGS. 7 and 8, two of the engagement portions 50 may be provided to coact with the ratchet teeth 20 being located on the first and second faces 24, 26.

It is noted that the spacing between the first and second ends 64, 66 affects force transmission from the actuator 48 to the plunger 12 particularly in the generation of torque. The spacing L between the first and second ends 64, 66, as well as the spacing S1, S2 of the engagement portion 50 from the first and second ends 64, 66, affects how torque is generated and transmitted to the plunger 12.

Figure 9:
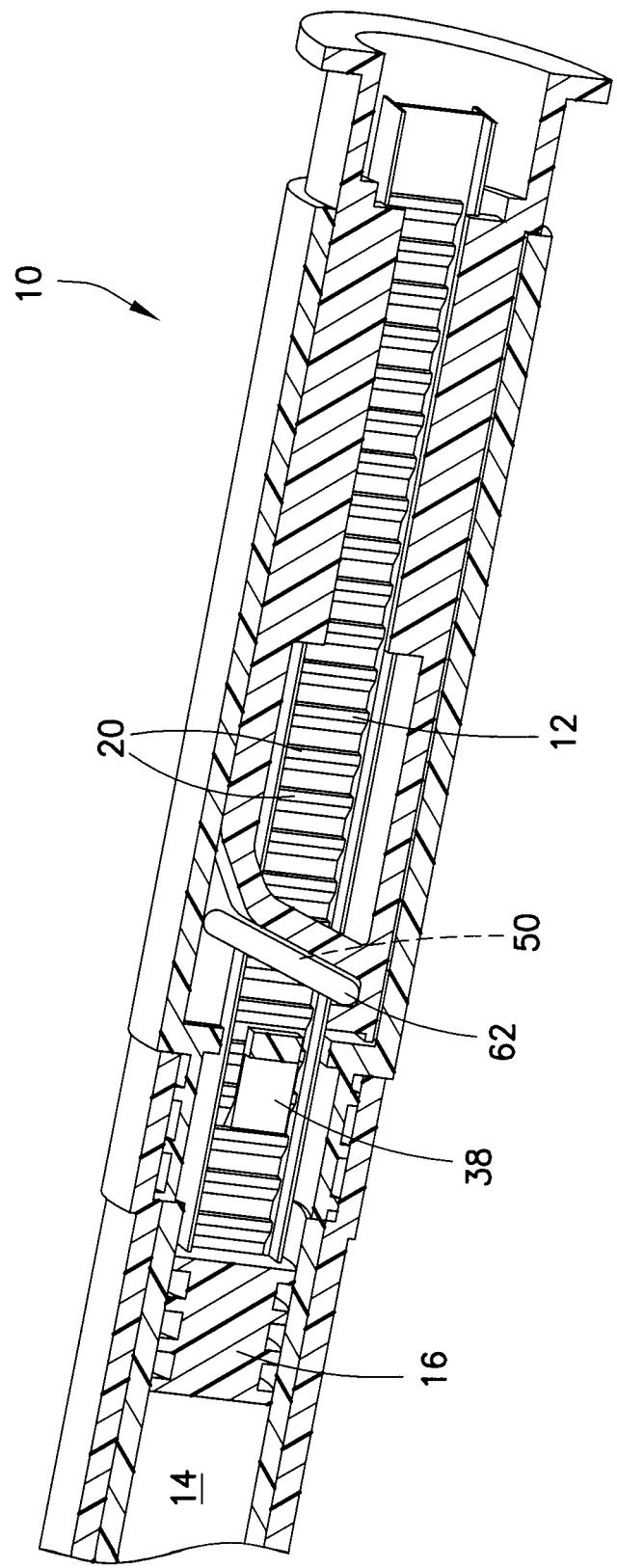

With reference to FIG. 9, the actuator 48 is shown in an initial pre-use state with the rocker 62 being inclined distally. With reference to FIG. 10, the actuator 48 has been advanced to the ready state with the rocker 62 having been drawn proximally with rotation about the second end 66 so as to be inclined in a proximal direction. During this movement, the engagement portion 50 bypasses one or more of the ratchet teeth 20 in the same manner as described above. As shown in FIG. 11, the actuator 48 is displaced from the ready state to cause actuation of the medical injector 10. With displacement of the actuator 48 from the ready state, the rocker 62 is caused to advance distally about the second end 66 with the engagement portion 50 causing the plunger 12 to also advance distally. Dose size may be restricted both by the key 58/channel 60 arrangement described above and/or by the range of motion of the rocker 62.

Figure 12:
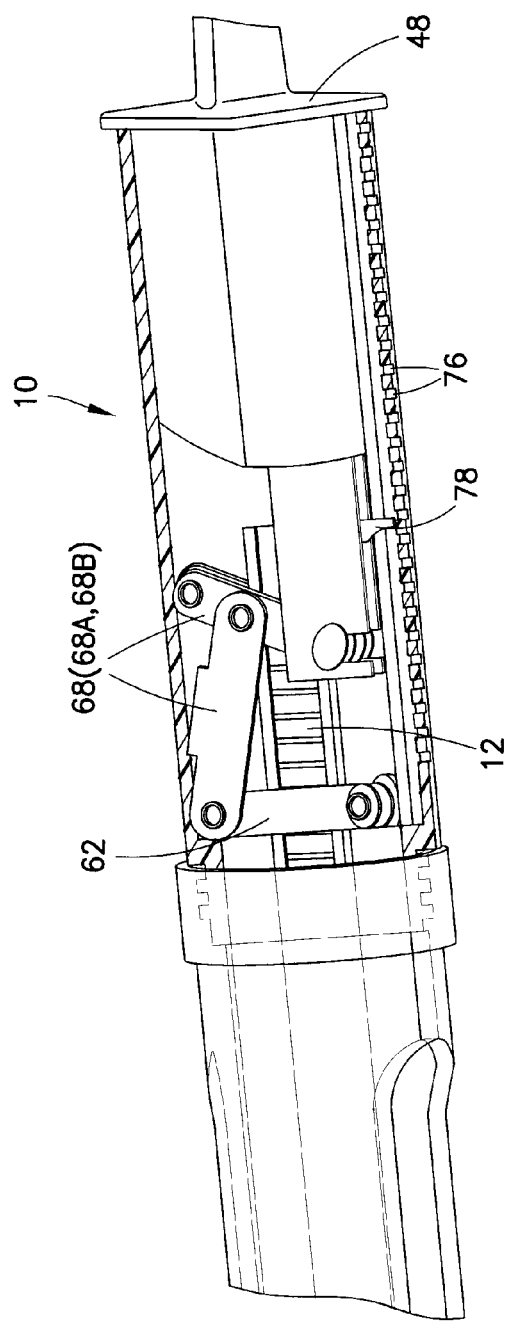
FIGS. 12 and 13 are perspective partial cross-sectional views illustrating the use of a multi-link rocker in accordance with an embodiment of the present invention.
Figure 13:
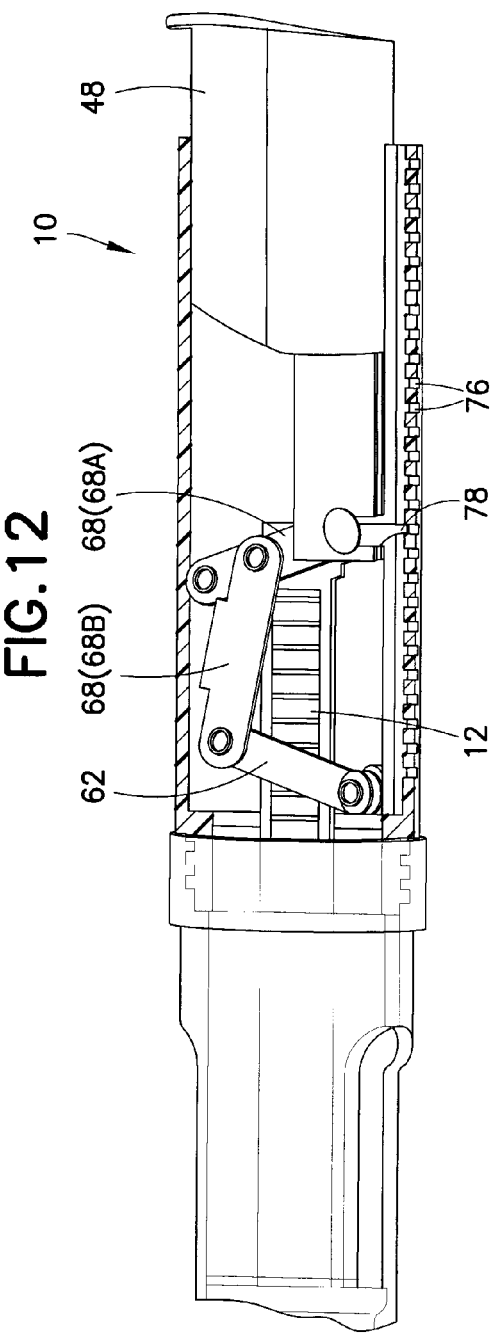

As will be appreciated by those skilled in the art, the rocker 62 may be directly coupled to the actuator 48, as shown in FIGS. 9-11. As will be appreciated by those skilled in the art, a multi-link arrangement may be used to couple the rocker 62 to the actuator 48. With reference to FIGS. 12 and 13, one or more links 68 may be connected between the rocker 62 and the actuator 48 to provide force for displacement thereof. Any arrangement of the links 68 may be utilized which transmits force from the actuator 48 to the rocker 62. As shown in FIGS. 12 and 13, two of the links 68 (68A, 68B) are utilized with the link 68A being pivotally connected to the actuator 48 and pivotally connected to the link 68B, and with the link 68B being pivotally connected to the link 68A and pivotally connected to the rocker 62. The links 68A, 68B collectively transmit force to the rocker 62.

Figure 15:
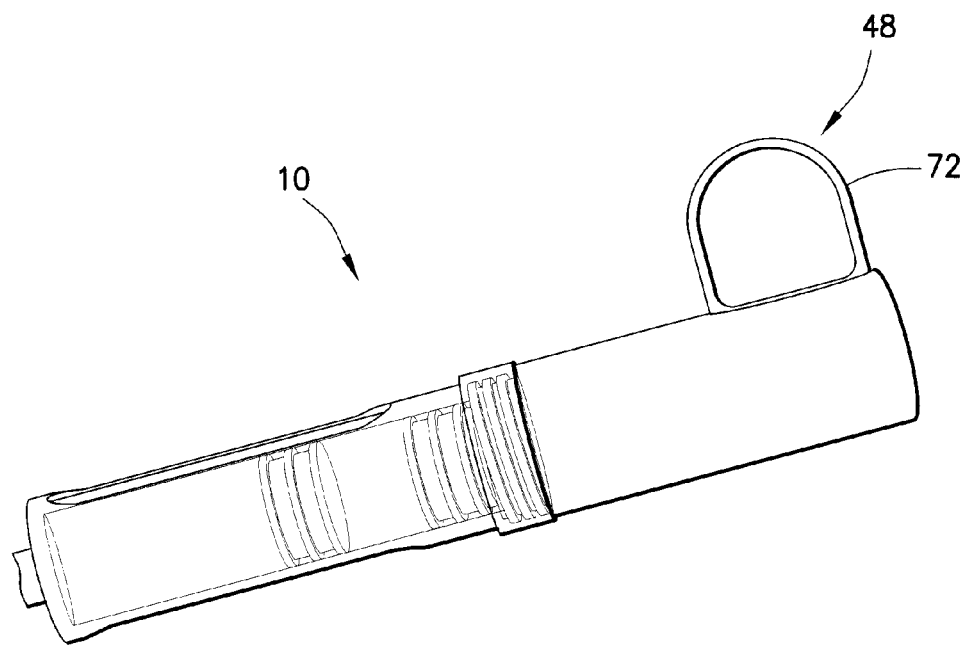
FIG. 15 is a partial perspective view of a pivotable actuator usable with the plunger of FIG. 2.
Figure 16:
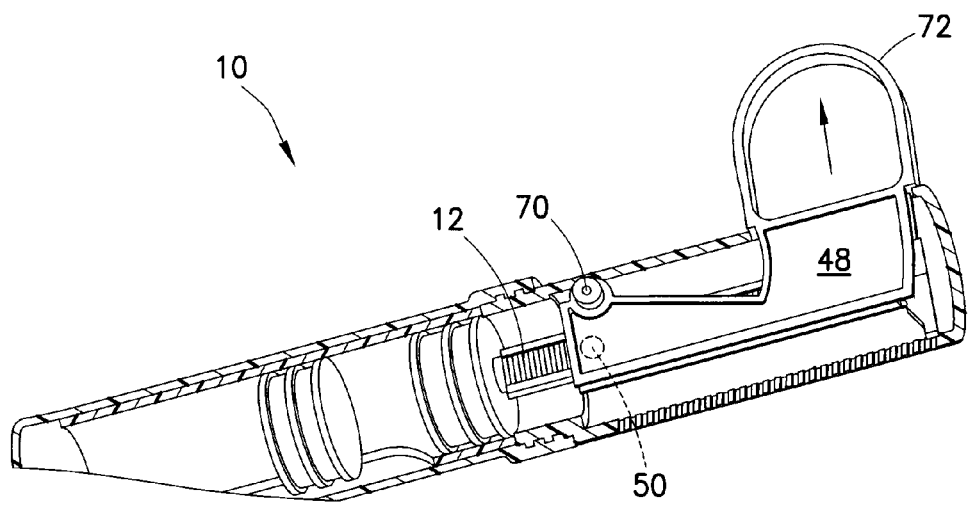
FIGS. 16 and 17 are perspective partial cross-sectional views illustrating use of the pivotable actuator of FIG. 15.
Figure 17:
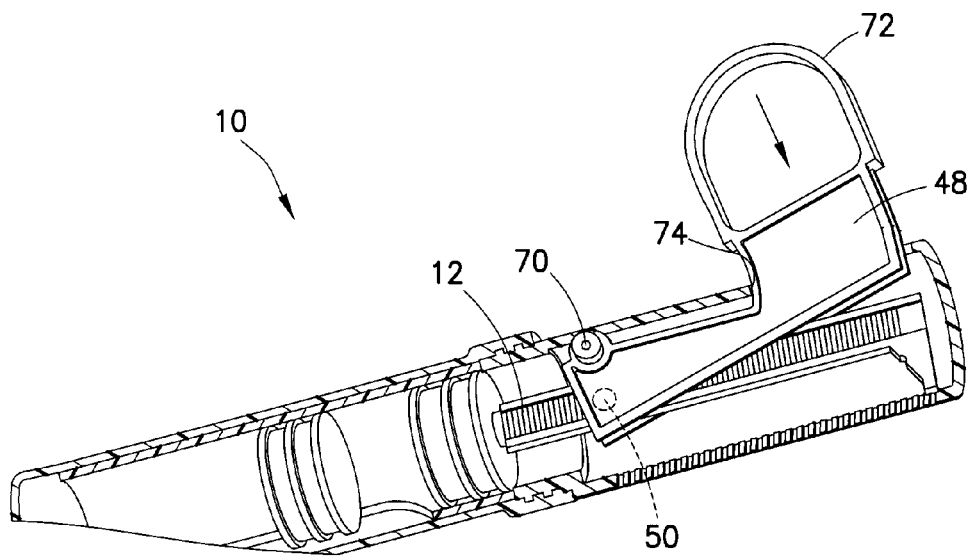

With reference to FIGS. 15-17, the actuator 48 may be arranged to be non-linearly displaced. As shown in FIGS. 15-17, the actuator 48 may be formed to pivot about a fulcrum 70. With the actuator 48 pivoting outwardly from the medical injector 10 about the fulcrum 70, the engagement portion 50 is caused to be displaced proximally. Conversely, inward pivoting of the actuator 48 about the fulcrum 70 causes distal displacement of the engagement portion 50. The engagement portion 50 coacts with the plunger 12 in the same manner as described above.

With reference to FIGS. 15 and 16, the medical injector 10 is shown in a pre-use state. To facilitate handling of the actuator 48, a grip ring or pad 72 may be provided which extends radially outwardly from the medical injector 10 to facilitate displacement of the actuator 48. To prepare for use, as shown by the arrow in FIG. 16, the actuator 48 is pivoted to a ready state as shown in FIG. 17. To cause actuation of the medical injector 10, the actuator 48 is pivoted inwardly from the ready state, as shown by the arrow in FIG. 17.

The size of the dose may be fixed with the actuator 48 being pivotable by limiting the range of rotation of the actuator 48. A portion 74 of the medical injector 10 may be configured to limit the range of rotation of the actuator 48, particularly outward rotation, such limited range corresponding to the ready state.

The actuator 48 may be formed as a linear slide actuator, but configured to accept a non-linear force to adjust the actuator 48 to the ready state. With reference to FIGS. 18-27, the actuator 48 may include a first portion 48A, formed in accordance with the description above. In addition, the actuator 48 may include a rotatable second portion 48B coupled to the first portion 48A so as to be rotatable relative thereto. This arrangement permits rotational adjustment of the actuator 48 to the ready state. Rotational adjustment is typical of pen-type injectors and may be preferred by some users.

The second portion 48B is accessible exteriorly of the medical injector 10 so as to be engageable from the outside by a user; particularly, the second portion 48B extends proximally from the proximal end 36 of the body 32. The first and second portions 48A, 48B are rotatably coupled in any known manner. By way of non-limiting example, the second portion 48B may be formed with a continuous ring 80 seated in channel 82 of the first portion 48A. The ring 80 is sized and shaped to rotate freely within the channel 82 with the first and second portions 48A, 48B being axially fixed to move together. As will be appreciated by those skilled in the art, the ring 80 and the channel 82 may be reversed on the first and second portions 48A, 48B.

Figure 19:
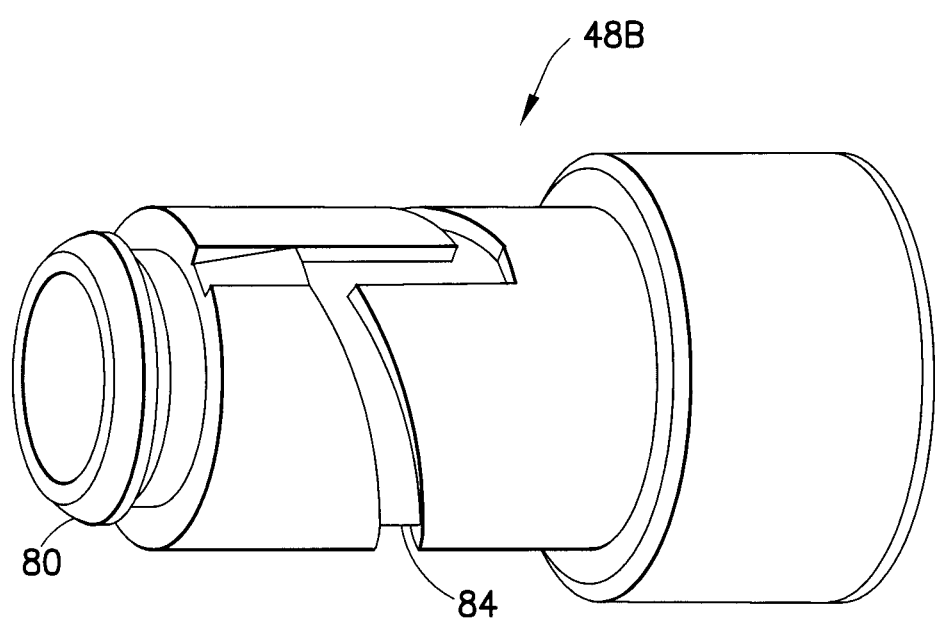
FIG. 19 is a perspective view of an embodiment of a second portion of an actuator of the medical injector of FIG. 18.

As shown in FIG. 19, a groove 84 is formed about an exterior of the second portion 48B. One or more keys 86 are located on surrounding portions of the medical injector 10, e.g., on the body 32, about the second portion 48B positioned and sized to be seated in the groove 84 so as to be moveable along the length thereof. The length of the groove 84 delimits the extent of rotation of the second portion 48B. According to one embodiment, the groove 84 is at least partially helical so as to have a screw thread shape. As will be appreciated by those skilled in the art, the key(s) 86 may be located on the exterior of the second portion 48B and the corresponding groove 84 may be formed on surrounding portions of the medical injector 10.

Rotation of the second portion 48B in a first rotational direction results in proximal displacement of the first and second portions 48A, 48B with corresponding proximal displacement of the engagement portion 50 to the ready state. In particular, rotation of the second portion 48B results in proximal displacement thereof and, in concert, proximal displacement of the first portion 48A and of the engagement portion 50. The first portion 48A is non-rotatably displaced proximally. The length of the groove 84 limits the extent of rotation of the second portion 48B thereby limiting the dose that may be administered. Once rotated to a set dose, the dose may be administered by pressing the second portion 48B, which results in distal advancement of the second portion 48B and, correspondingly, distal non-rotating advancement of the first portion 48 along with the engagement portion 50.

Figure 21:
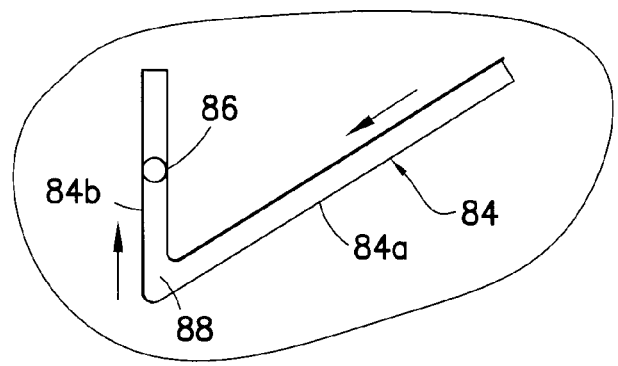
FIGS. 21 and 22 illustrate alternative embodiments of grooves of the second portion of FIG. 19.

With distal advancement of the second portion 48B, it is preferred that the second portion 48B be advanced linearly without rotation. To this end, it is preferred that the groove 84 be formed with a first helical portion 84a and a second axial portion 84b extending from the first helical portion 84a generally parallel to the longitudinal axis of the second portion 48B. Referring to FIG. 21, with this arrangement, the one or more keys 86 traverse the first helical portion 84a with rotation of the second portion 48B in a proximal direction. Elbow 88 is defined at the junction of the first helical portion 84a and the second axial portion 84b which limits the extent of rotation and, thus, proximal displacement of the second portion 48B. The elbow 88 defines the ready position of the actuator 48. For actuation, the second portion 48B is depressed and caused to advance distally linearly without rotation with the one or more keys 86 traversing the second axial portion 84b. This, in turn, causes distal advancement of the first portion 48A and distal advancement of the plunger 12 through engagement with the engagement portion 50. The linear displacement of the second portion 48B permits force applied thereto to be fully transmitted in one axial direction, without resolution into two or more components. As such, the full force of actuation applied to the second portion 48B is transmitted to the actuator 48.

Figure 22:
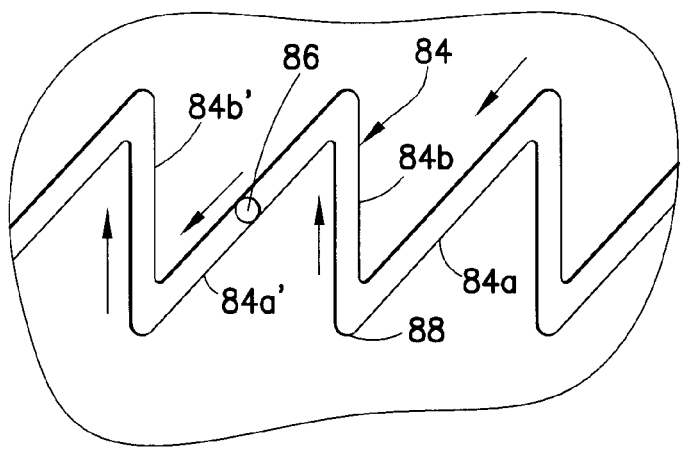

For a single-dose version of this arrangement, a single set of the first helical portion and the second axial portion 84a, 84b may be utilized. For multiple dosing, as shown in FIG. 22, the groove 84 may be extended such that a secondary helical portion 84a' may extend directly from the terminus of the second axial portion 84b which extends into a secondary axial portion 84b' and so forth as needed. According to one embodiment, a series of the first helical portions 84a and second axial portions 84b may be defined continuously about the second portion 48B to facilitate multiple dosing. According to one embodiment more than one groove 84 may be utilized with a corresponding set of one or more keys 86. Also, one or more of the grooves 84 and one or more of the keys 86 may be located on the second portion 48B and/or surrounding portions of the medical injector 10.

Figure 23:
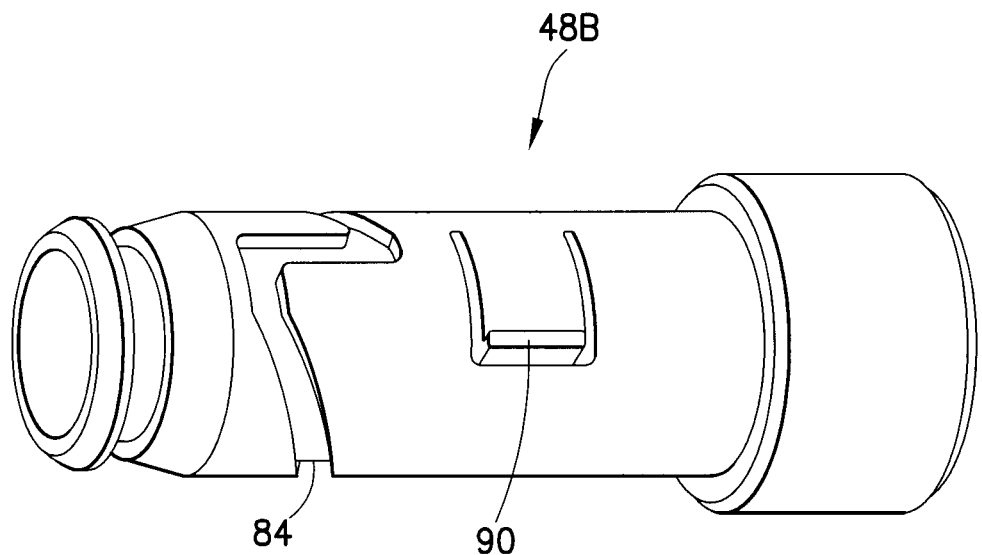
FIG. 23 is a perspective view of another embodiment of a second portion of the actuator of the medical injector of FIG. 18.
Figure 24:
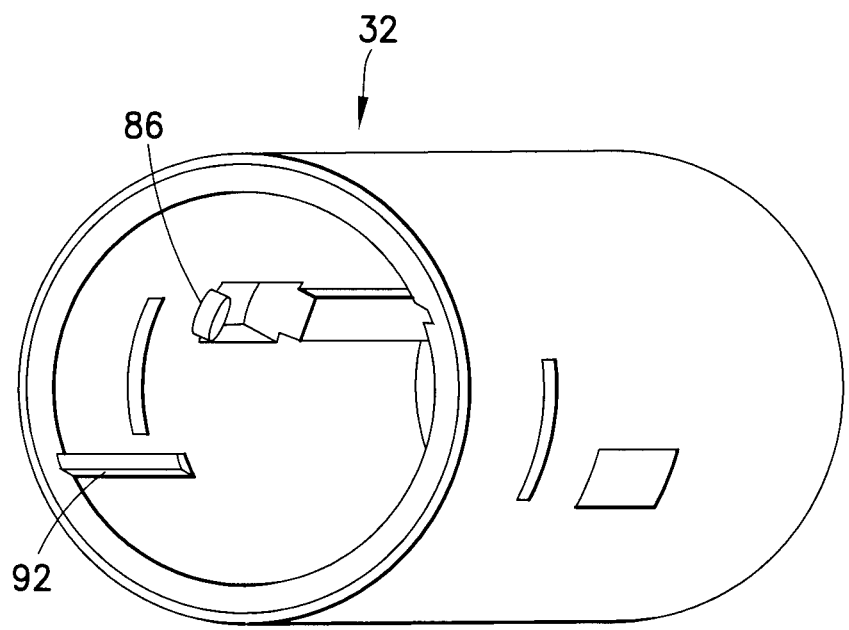
FIG. 24 is a perspective view of a body of the medical injector of FIG. 18.

Preferably, reverse rotation of the second portion 48B should be avoided. To this end, as shown in FIGS. 23-24, one or more detents 90 may be formed on the second portion 48B formed to snap engage one or more locating channels 92 formed on the medical injector 10 about the second portion 48B, such as on the body 32. Preferably, a locating channel 92 is located corresponding to the second portion 48B being in the ready position, and such a ready position locating channel 92 is elongated such that the detent 90 may be displaced along the length thereof with the second portion 48B during dose administration. As will be appreciated by the skilled in the art, the detent(s) 90 may be formed on the medical injector 10 and the locating channels may be formed on the second portion 48B.

Figure 25:
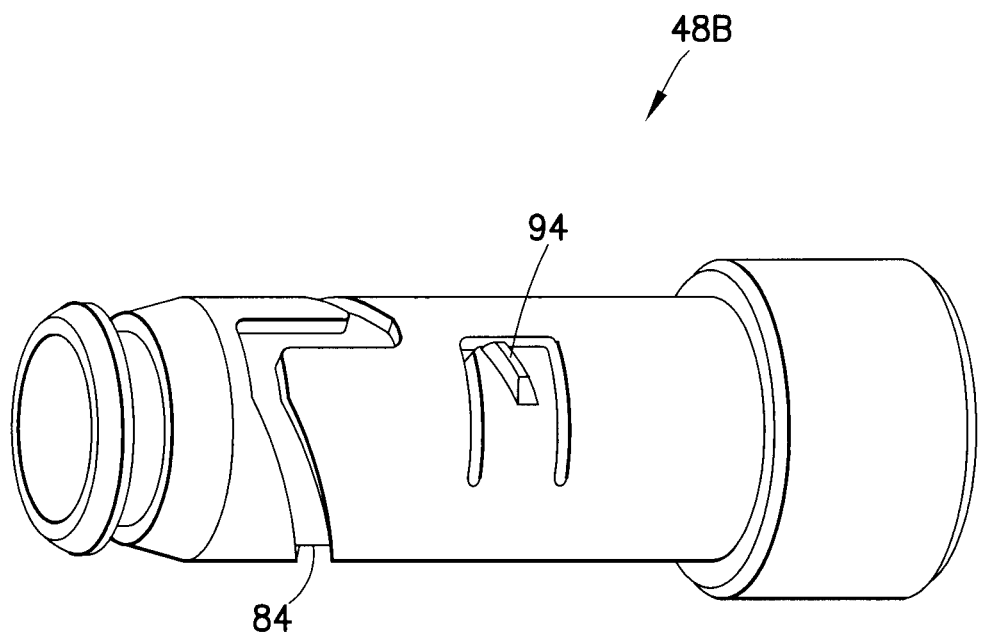
FIG. 25 is a perspective view of yet another embodiment of the second portion of the actuator of the medical injector of FIG. 18.
Figure 26:
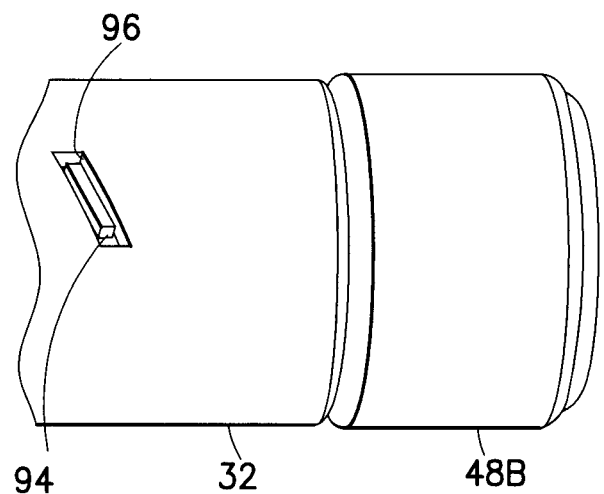
FIG. 26 is a partial perspective view of the medical injector of FIG. 18 with the second portion of FIG. 25.
Figure 30:
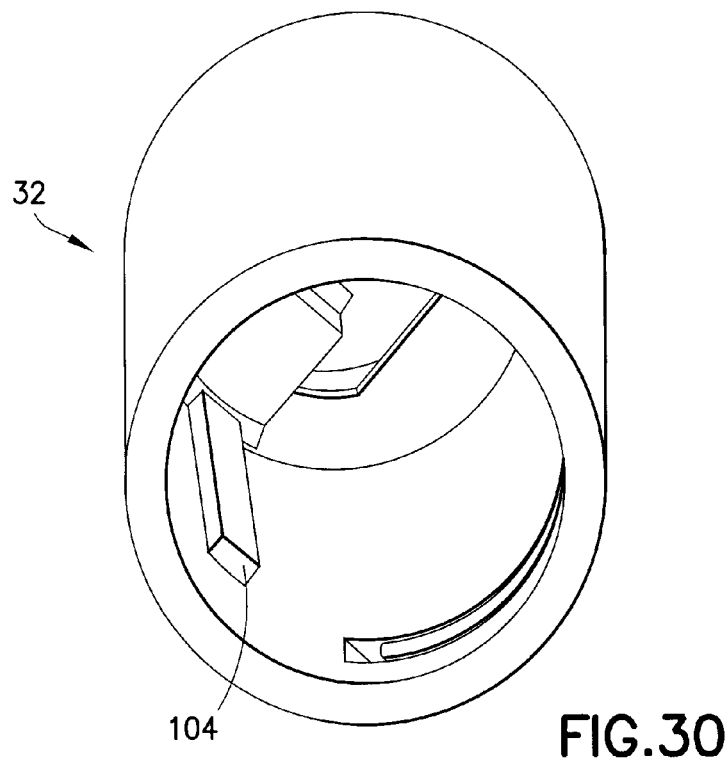
FIGS. 30 and 31 are perspective views of a body of the medical injector of FIG. 28.

In addition, reverse axial movement along the second axial portion 84b, particularly after injection, is undesired. To this end, as shown in FIGS. 25 and 26, a locking tab 94 is provided on the second portion 48B which is configured to snap engage into a locking channel 96 at a position coinciding with an end of the injection (e.g., position coinciding with the one or more keys 86 reaching the terminus of the second axial portion 84b at the end of a dosing stroke). Axial movement of the second portion 48B is thus limited. The locking channel 96 may be configured to permit rotation of the locking tab 94 for separation therefrom with rotation of the second portion 48B in preparing for a subsequent dose. The locking channel 96 is formed on a surrounding portion of the medical injector 10, such as on the body 32. As will be appreciated by those skilled in the art, the locking tab 94 may be formed on the medical injector 10 and the locking channel 96 may be provided on the second portion 48B.

Figure 27:
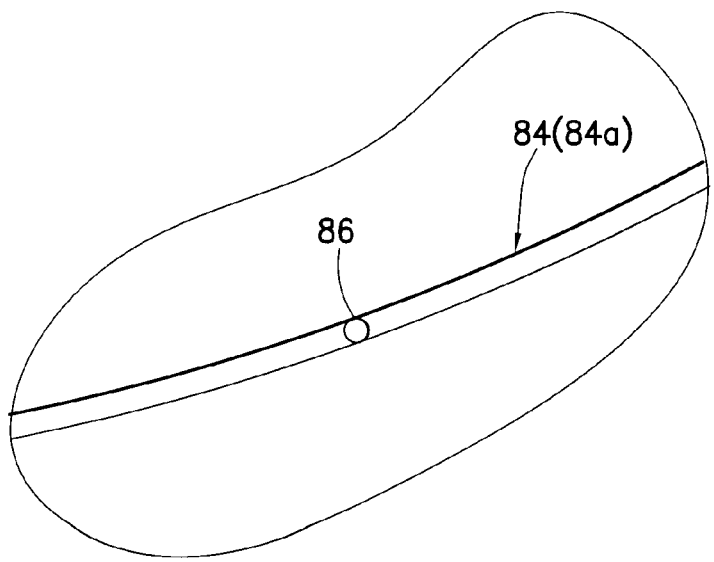
FIG. 27 illustrates another embodiment of a groove of the second portion of FIG. 19.

Further, as will be appreciated by those skilled in the art, with the arrangement discussed above, particularly with the use of the first and second portions 84a, 84b of the groove 84, doses are fixed doses. According to one embodiment to allow for variable dosing, the second portion 48B may be allowed to rotate during distal advancement of the second portion 48B with the one or more keys 86 traveling along the groove 84. Thus, in this embodiment, as shown in FIG. 27, only the helical portion 84a of the groove 84 need be provided. With this arrangement, the second portion 48B may be rotated to any location along the groove 84 (84a) to set a dose with reverse rotation along the groove 84 (84a) permitting dosing. A scale, or other index, as known in the art may be provided to correspond to rotational displacement of the second portion 48B to provide indication of the set dose amount. To limit unwanted reverse rotation, and to retain position at a set dose, a releasable retention arrangement, as is in known in the art, may be utilized.

The first and second portions 48A, 48B may be utilized with any of the features described herein. Preferably, the first and second portions 48A, 48B are used in conjunction with the rocker 62.

FIG. 28 is a perspective view of the medical injector 10 in accordance with another embodiment of the present invention. With reference to FIGS. 28-33, medical injector 10 includes a body 32, a rotary knob 100 rotatably connected to the body 32, an actuator 48 disposed within the body 32, and a cap 101 connected to the actuator 48. As shown in FIG. 29, the actuator 48 includes the groove 84 as described above. The actuator 48 also includes an axial groove 102. The axial groove 102 interacts with an axial key 104 (shown in FIG. 30) disposed on an interior of the body 32 to guide axial movement of the actuator 48 with respect to the body 32 and prevent rotation of the actuator 48 with respect to the body 32. As will be appreciated by those skilled in the art, the axial groove 102 may be disposed on the interior of the body 32 and the axial key 104 may be disposed on the actuator 48, without departing from the scope of the invention.

Figure 31:
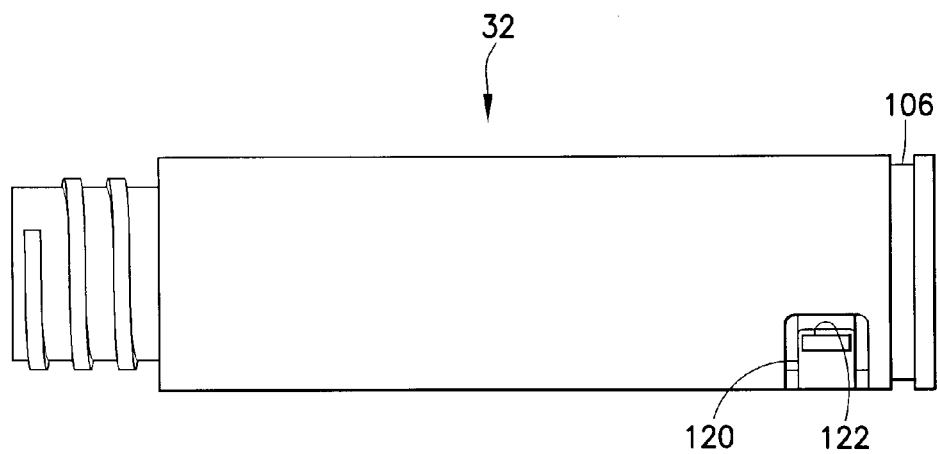

As shown in FIG. 31, the body 32 also includes a circumferential groove 106 disposed at a proximal end thereof for connection with the rotary knob 100, as will be described in greater detail below. Additionally, as will be described in greater detail below, the body 32 includes a cantilevered, circumferential arm 120 with a triangular protrusion 122 disposed at an end thereof and protruding radially outward.

Figure 32:
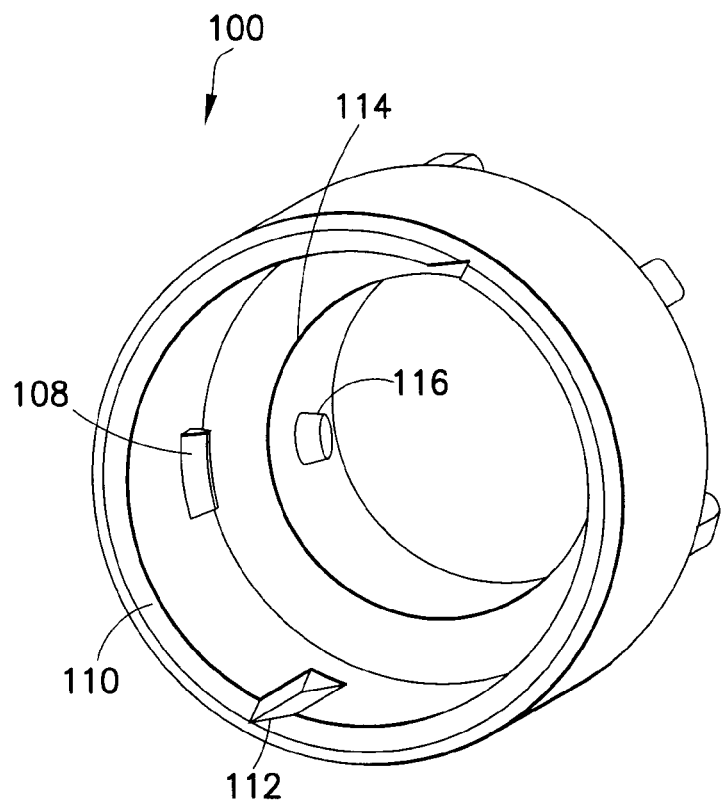
FIGS. 32 and 33 are perspective views of a rotary knob of the medical injector of FIG. 28.
Figure 33:
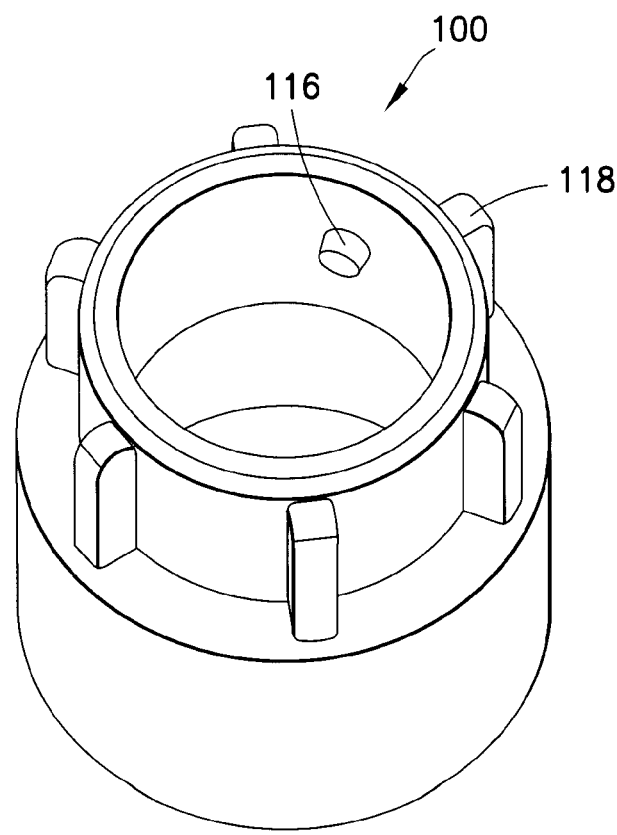

FIG. 32 is a perspective view of the distal end of the rotary knob 100 and FIG. 33 is a perspective view of the proximal end of the rotary knob 100. As shown in FIG. 32, the rotary knob 100 includes a circumferentially extending and radially inward protruding connector 108. According to one embodiment, the connector 108 is substantially wedge-shaped. To assemble the medical injector 10, the rotary knob 100 is distally inserted over the proximal end of the body 32 until the connector 108 slips into the circumferential groove 106 of the body 32, connecting the rotary knob 100 to the body 32. The wedge shape of the connector 108 secures the rotary knob 100 to the body 32, substantially preventing proximal displacement of the rotary knob 100 relative to the body 32 while permitting rotation of the rotary knob 100 relative to the body 32.

As shown in FIG. 32, the connector 108 is disposed in a large diameter portion 110 of the rotary knob 100. Also disposed in the large diameter portion 110 of the rotary knob 100 is a triangular groove 112. The triangular groove 112 interacts with the triangular protrusion 122 on the arm 120 to permit unidirectional rotation of the rotary knob 100 with respect to the body 32. That is, the triangular groove 112 and the triangular protrusion 122 interact to permit rotation of the rotary knob 100 only in a direction to advance the plunger 12 proximally. The rotary knob 100 also has a reduced diameter portion 114 which prevents proximal displacement of the rotary knob relative to the body subsequent to connection between the connector 108 and the circumferential groove 106. Additionally, a camming projection or key 116 projects radially inward from the reduced diameter portion 114. Similar to the key 86 described above, the key 116 interacts with the groove 84 of the actuator 48 to convert rotational movement of the rotary knob 100 into proximal axial movement of the actuator 48. Subsequent to the proximal axial movement of the actuator 48, the user depresses the cap 101 (connected to the actuator 48) to distally displace the actuator 48 relative to the body 32, and thus distally advance the plunger 12.

Referring to FIG. 33, the rotary knob 100 also includes radially outward projecting ribs 118 at a proximal end thereof. The ribs 118 function as a user interface for the user to grasp and rotate the rotary knob 100.

Figure 14:
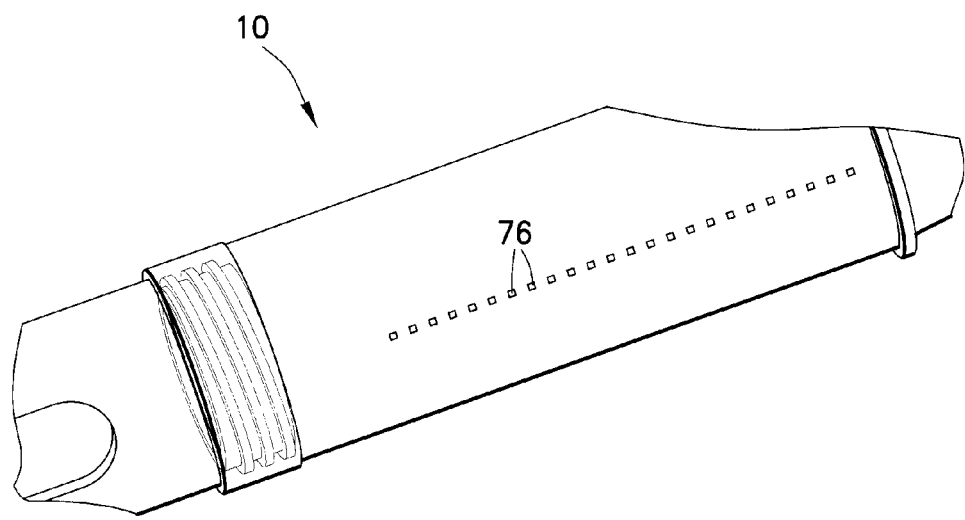
FIG. 14 shows a dose counter usable with an embodiment of the present invention.

As will be appreciated by those skilled in the art, the medical injector 10 may be utilized with various features. With reference to FIGS. 12-14, a dose counter may be provided with the medical injector 10 which gives an indication of the number of available doses to be administered. For example, a series of dose indicating holes 76 may be formed in the medical injector 10, particularly to be visible from the outside thereof. A pointer 78 may be provided on the actuator 48 and formed to be visible through a single one of the dose indicating holes 76 in a given instance. During use, with the plunger 12 being distally advanced dose by dose, the pointer 78 is likewise advanced along the series of the dose indicating holes 76. According to one embodiment, the number of the dose indicating holes 76 located distally of the pointer 78 provides as an indication of the remaining number of doses. With the pointer 78 appearing in the distal-most of the dose indicating holes 76, indication is provided that no remaining doses are available for administration.

It is preferred that the pointer 78 be formed of a contrasting color relative to the portion of the medical injector 10 located about the dose indicating holes 76, so that the pointer 78 is readily visible through the dose indicating holes 76.

Figure 34:
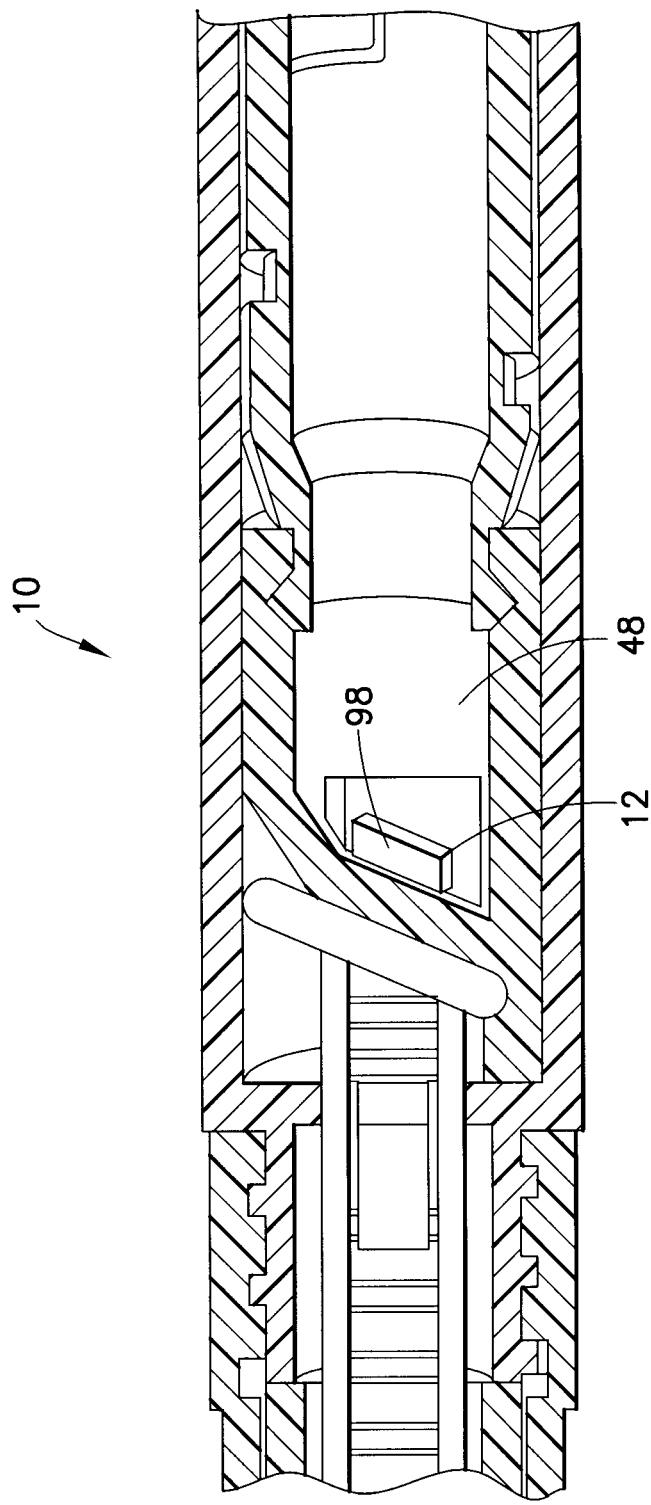
FIG. 34 is a partial cross-sectional view of a limiter rib for preventing dose setting beyond an available amount.

In addition, according to one embodiment shown in FIG. 34, a protruding limiter rib 98 may extend from a distal portion of the plunger 12 located to coincide with the dosage setting on the plunger 12 corresponding to the last amount of available drug in the reservoir 14. Accordingly, with a predetermined extent of distal advancement of the plunger 12, the limiter rib 98 is formed to interferingly engage a portion of the actuator 48 and block proximal movement therepast. In this manner, a dose greater than the available amount in the reservoir 14 cannot be set by the actuator 48.

Figure 35:
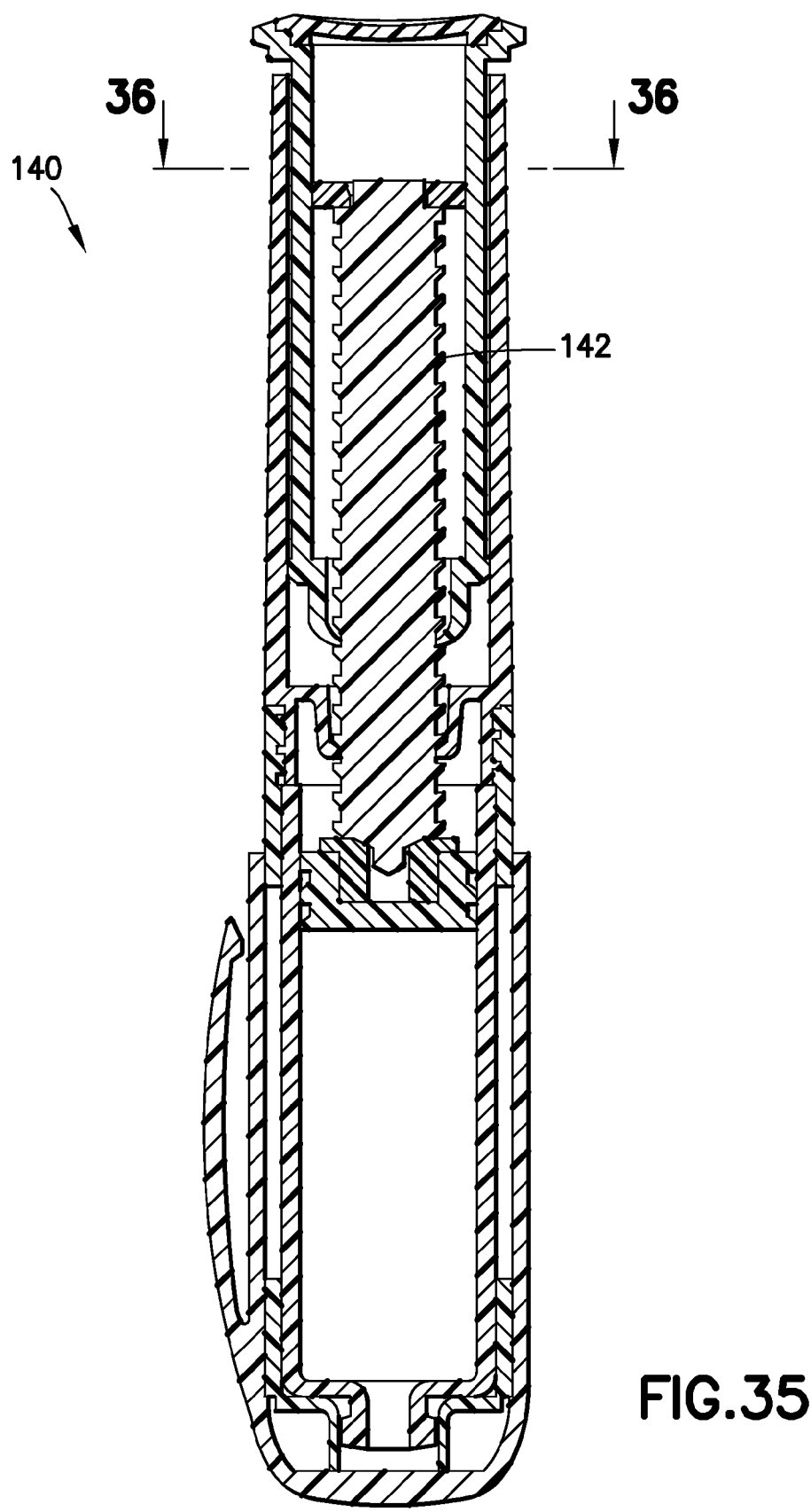
FIG. 35 is a cross-sectional view of a medical injector in accordance with another embodiment of the present invention.
Figure 36:
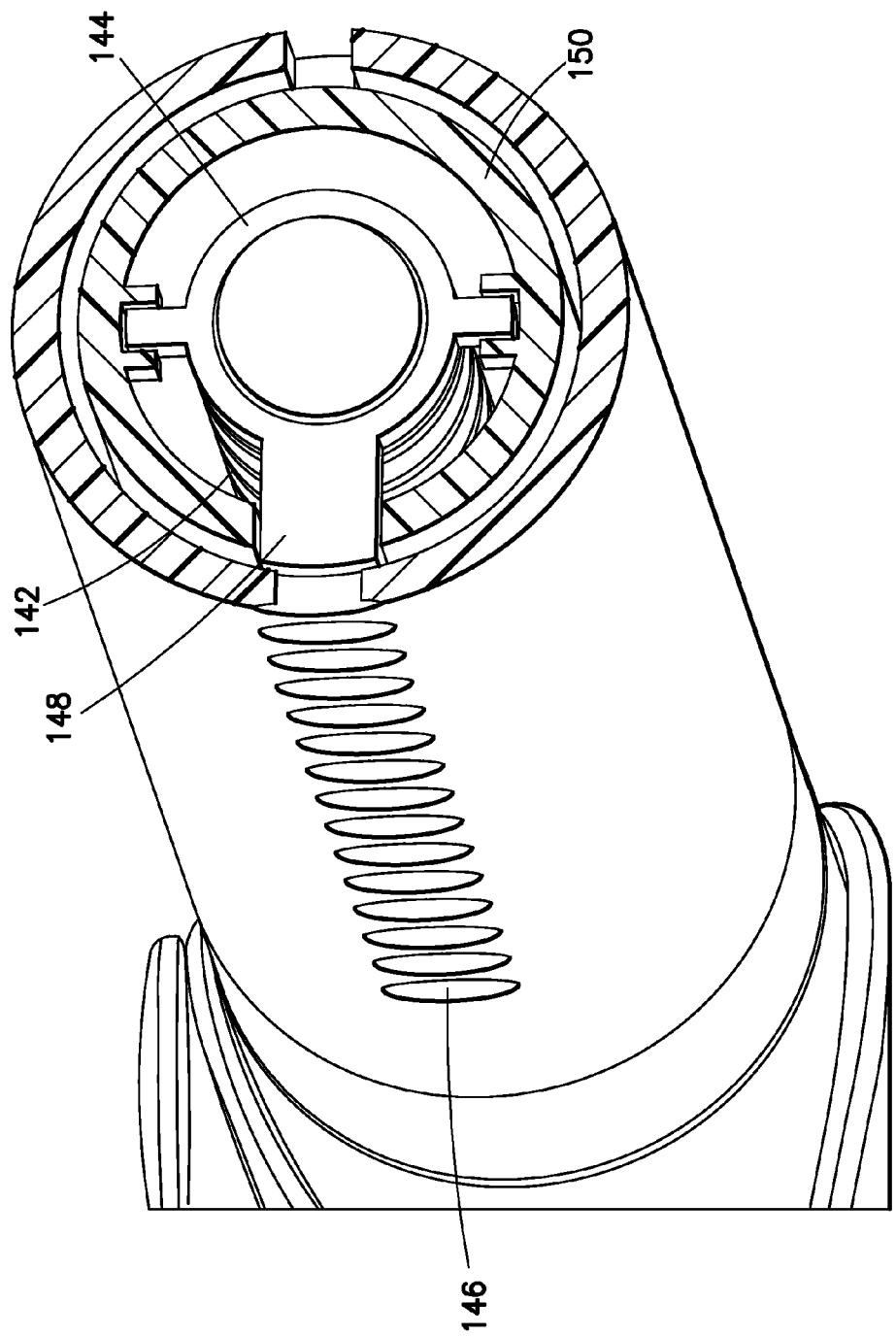
FIG. 36 is a perspective cross-sectional view of the medical injector of FIG. 35 taken along line 36-36 of FIG. 35.

In the above-described embodiments, the plunger 12 is substantially flat. In contrast, in the following embodiments, the plungers are substantially cylindrical. For example, in the medical injector 140 shown in FIGS. 35 and 36, the plunger 142 is substantially cylindrical and the ratchet teeth extend circumferentially around the plunger 142. In such an embodiment, the orientation of the plunger is not critical, thereby easing assembly of the device. In addition, as shown in FIGS. 35 and 36, a pointer or indicator flag 144 connected to the plunger 142 is visible to a user through indicating holes 146 to indicate the dosage. The pointer 144 engages an axial slot 148 in the actuator 150 to provide an alignment feature.

Figure 37:
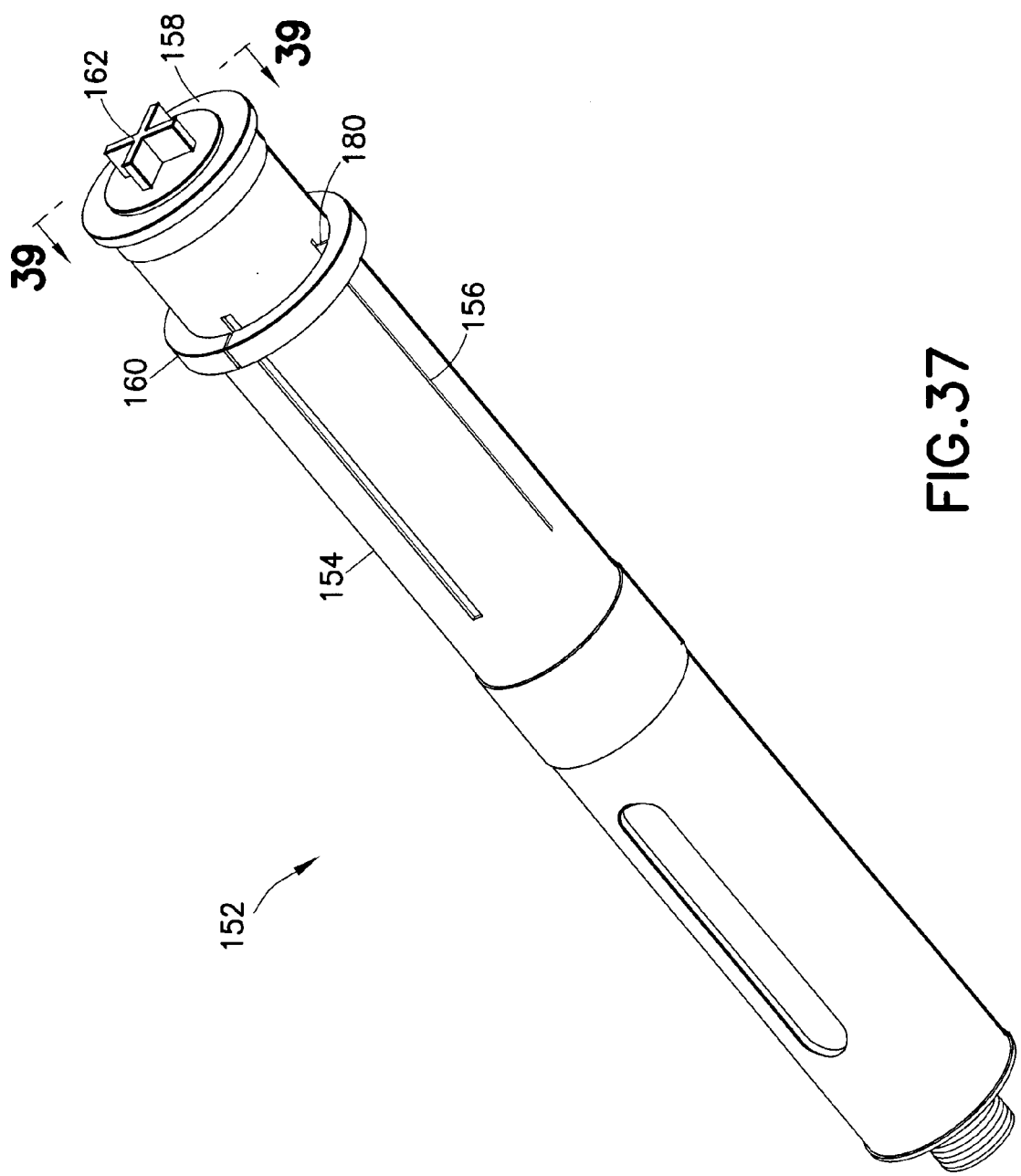
FIG. 37 is a perspective view of a medical injector according to another embodiment of the present invention.
Figure 38:
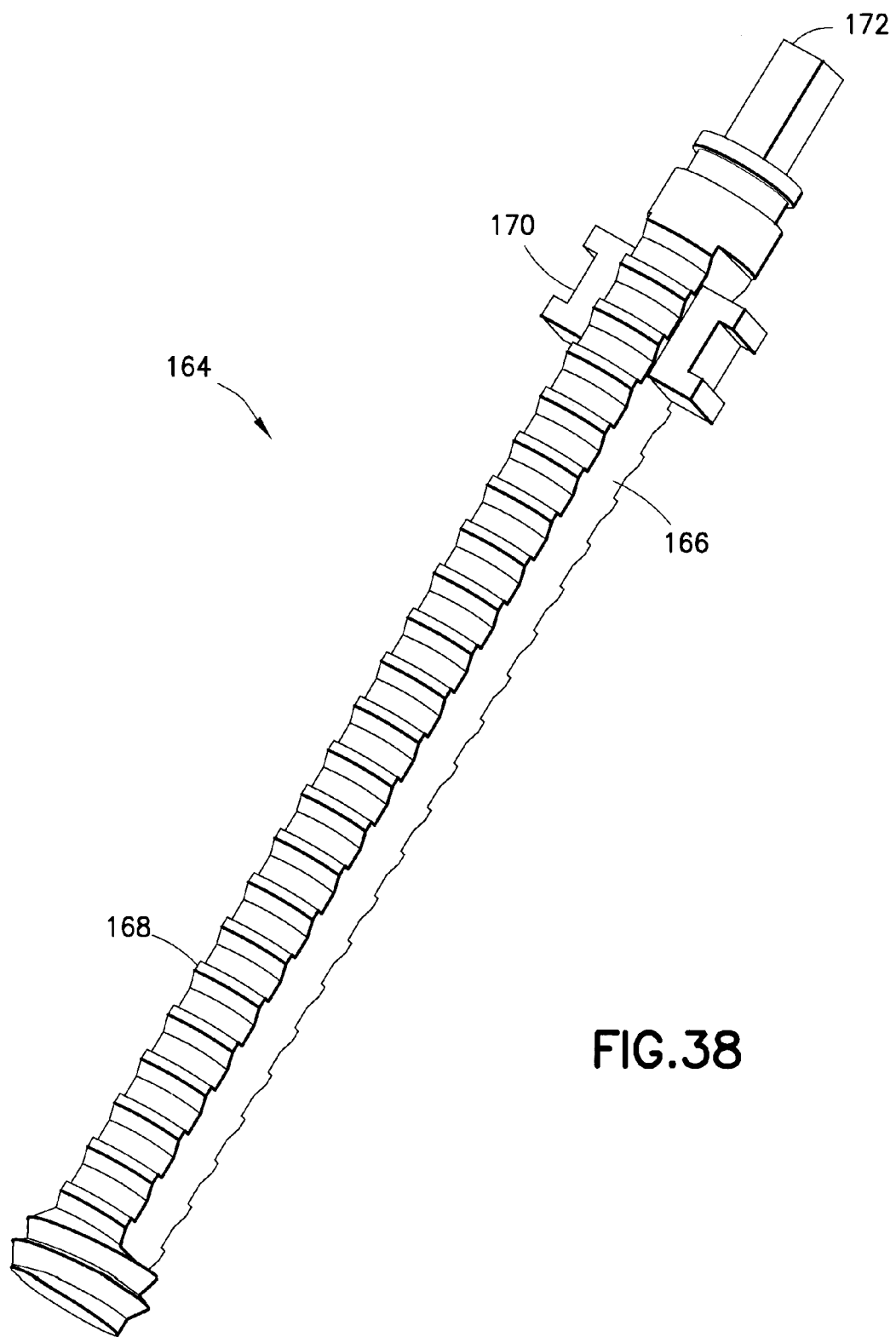
FIG. 38 is a perspective view of a plunger usable with the medical injector of FIG. 37.
Figure 39:
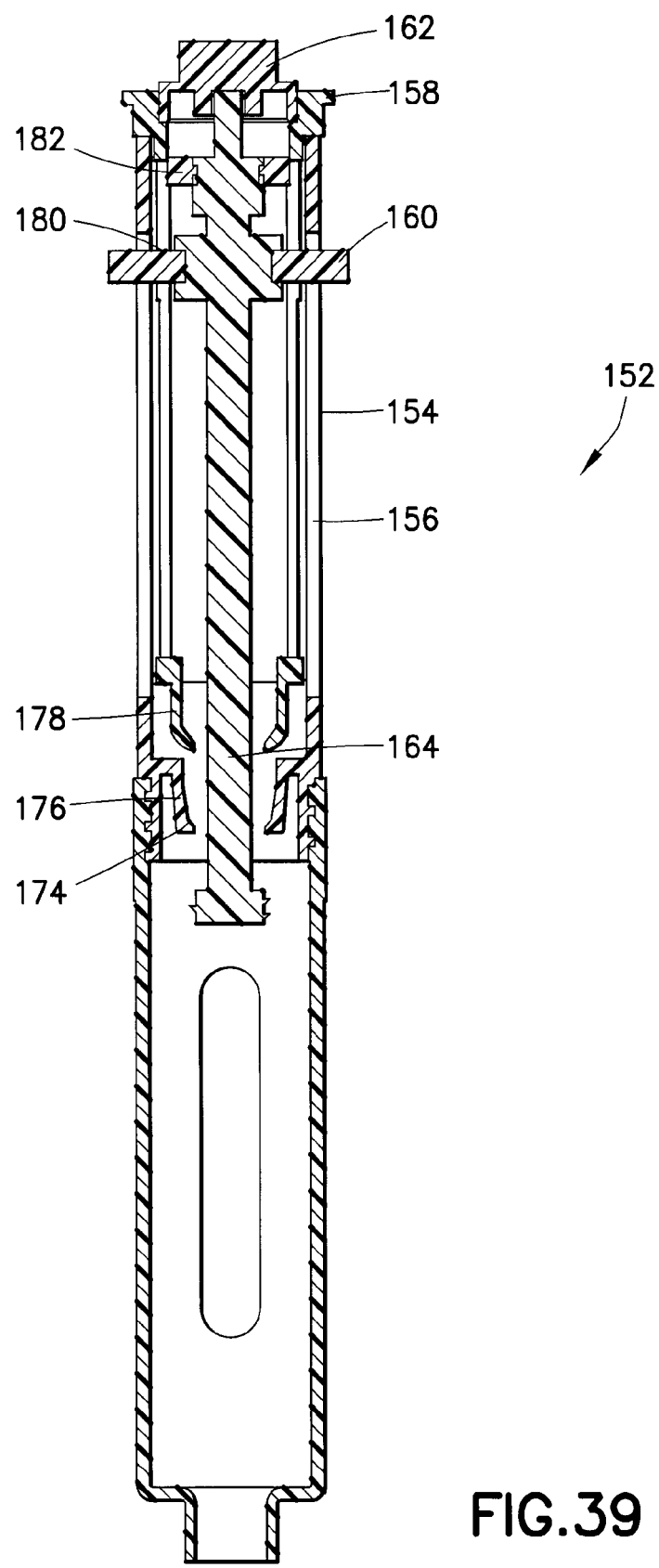
FIG. 39 is a cross-sectional view of the medical injector of FIG. 37 taken along line 39-39 of FIG. 37.

FIG. 37 illustrates a medical injector 152 according to another embodiment of the present invention, FIG. 38 is a perspective view of a plunger usable with the medical injector 152, and FIG. 39 is a cross-sectional view of the medical injector 152. As shown in FIGS. 37 and 39, the medical injector 152 includes a body 154 having axial slots 156 therein, an actuator 158, a plunger slider or ring slider 160 with arms extending through the slots 156, and a mode selector 162. According to one embodiment, the ratchet teeth on the plunger are circumferentially discontinuous. Put another way, at least one portion of the plunger is axially free of ratchet teeth. FIG. 38 illustrates another embodiment of a cylindrical plunger 164 in which the plunger 164 is frusto-cylindrical. In other words, the plunger 164 has a pair of flat sides 166. As with the plunger 12, the plunger 164 also has a plurality of spaced-apart ratchet teeth 168 disposed along the length thereof. The plunger 164 also has a pair of ring slider connectors 170 disposed on the flat sides 166 and a mode selector connector 172 disposed at a proximal end of the plunger 164. The illustrated mode selector connector 172 is substantially square. One skilled in the art will appreciate that other shapes may be used without departing from the scope of the present invention. For example, the mode selector connector 172 may be triangular, rectangular, pentagonal, or hexagonal, or may have more sides.

The mode selector 162 has a recess corresponding to the mode selector connector 172 to engage the mode selector connector 172. While in the illustrated embodiment, the male protrusion (mode selector connector 172) is disposed at the proximal end of the plunger 166 and the corresponding female recess is disposed on the distal end of the mode selector 162, one skilled in the art will appreciate that the male protrusion may be disposed on the distal end of the mode selector 162 and the corresponding female recess may be disposed on the proximal and of the plunger 166 without departing from the scope of the present invention. The mode selector 162 is rotatably disposed with respect to the actuator 158, and thereby, as described in greater detail below, provides an interface for a user to rotate the plunger 166.

Similar to the embodiments described previously, in one orientation, the ratchet teeth 168 of the plunger 166 engage the pawls 174 of the indexer 176 and the engagement pawls 178 of the actuator 158. But because of the design of the plunger 164 (including the flat sides 166), the plunger 164 is rotatable with respect to the body 154. Accordingly, using the mode selector 162, a user can rotate the plunger 164 to an orientation in which the ratchet teeth 168 are disengaged from the pawls 174 and the engagement pawls 178, and the flat sides 166 are aligned with the pawls 174 and the engagement pawls 178, as shown in FIG. 39. Such an alignment permits selective, free distal and proximal displacement of the plunger 164. This feature is useful, for example, for reconstituting a lyophilized medicament, which will be discussed in greater detail below.

According to one embodiment, the ring slider connectors 170 disposed on the flat sides 166 of the plunger 164 selectively engage the arms 180 of the ring slider 160 that extend inwardly through the slots 156 of the body 154. For example, when a user rotates the mode selector 162 to disengage the ratchet teeth 168 from the pawls 174 and the engagement pawls 178, the ring slider connectors 170 rotate into engagement with the arms 180 of the ring slider 160. The user then can use the ring slider 162 to control displacement of the plunger 164.

As shown in FIG. 39, medical injector 152 also includes a pointer 182 for indicating the dosage, similar to the pointer 144. According to another embodiment, in which the axial slots 156 are circumferentially enlarged to accommodate rotation of the ring slider 160, the plunger 164 is fixedly connected to the ring slider 160, which serves as a dosage indicator.

Figure 40:
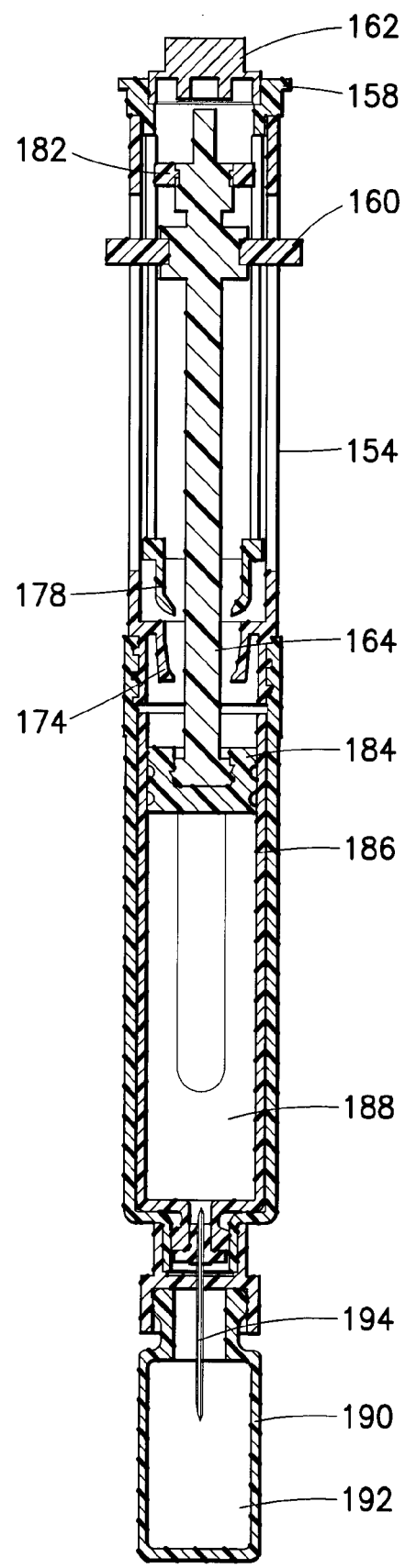
FIG. 40 is a cross-sectional view illustrating the operation of the medical injector of FIG. 37.

Reconstitution of a lyophilized medicament will now be described with reference to FIG. 40. The stopper 184 is disposed on the distal end of the plunger 164 inside a cartridge 186 containing a diluent 188 therein. The medicament container 190 with a lyophilized medicament 192 disposed therein is connected to a distal end of the cartridge 186 with a double-ended needle 194 communicating between interior of the medicament container 190 and the cartridge 186. After the user rotates the mode selector 162 to disengage the ratchet teeth 168 from the pawls 174 and the engagement pawls 178, the user distally slides the ring slider 160, thereby distally displacing the plunger 164 and the stopper 184, and expelling the diluent 188 into the medicament container 190. Subsequent to the reconstitution of the lyophilized medicament 192, the user proximally slides the ring slider 160, thereby proximally displacing the plunger 164 and the stopper 184, and drawing the reconstituted medicament into the cartridge 186. Thereafter, the user disconnects the medicament container 190 and rotates the mode selector 162 to reengage the ratchet teeth 168 with the pawls 174 and the engagement pawls 178. At this point, the reconstituted medicament can be injected as described above.

Figure 41:
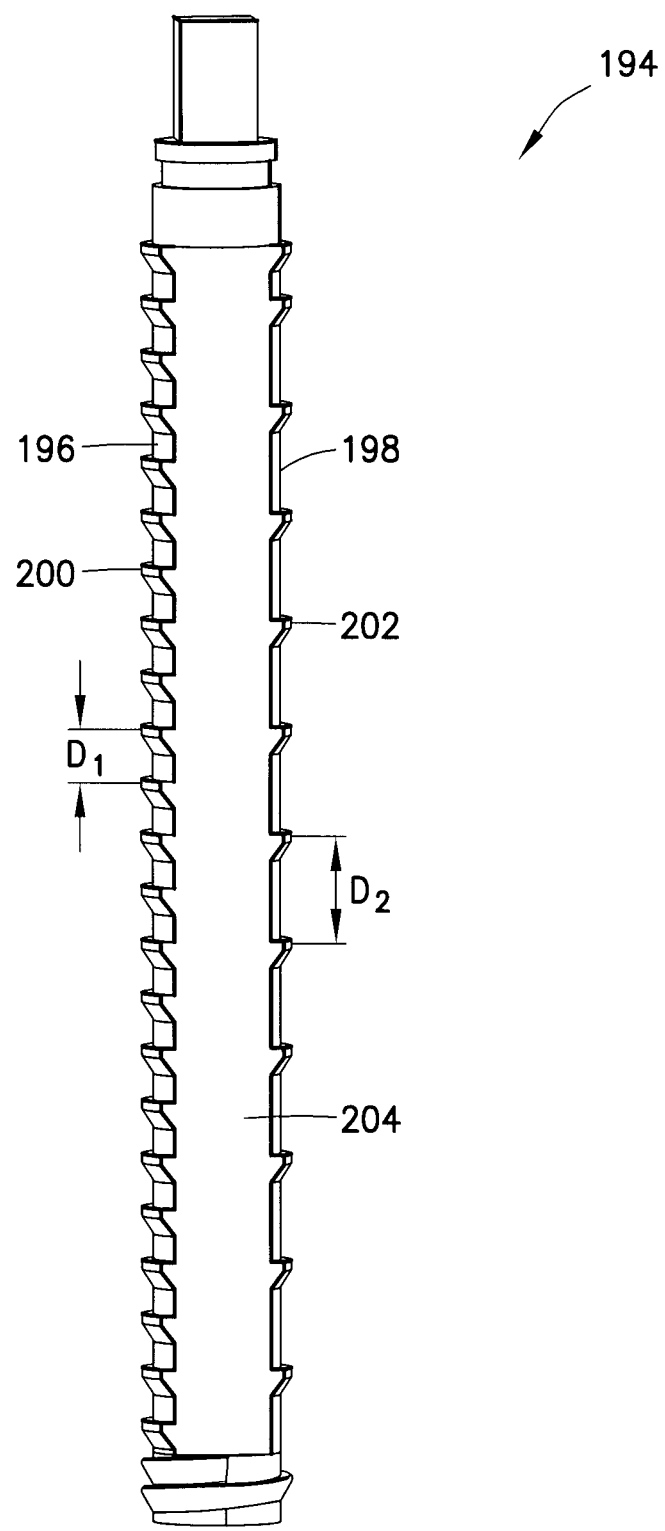
FIG. 41 is a perspective view of another embodiment of a plunger usable with the medical injector of FIG. 37.

In the medical injector employing a ratchet plunger similar to those described above, discrete dosage settings are determined by the pitch of (or spacing between) the ratchets. FIG. 41 is a perspective view of the plunger 194 in accordance with another embodiment of the present invention in which a user may select one of a plurality of predetermined ratchet spacings. As shown in FIG. 41, the plunger 194 has two sides with and 196 and 198 with respective pluralities of spaced-apart ratchet teeth 200 and 202 disposed along the length thereof. The distance between ratchet teeth 200 is shown as $D_1$ and the distance between ratchet teeth 202 is shown as $D_2$, which is greater than $D_1$. The plunger 194 is rotatable with respect to the body 154 and the actuator 158 so that a user can select a desired spacing between ratchet teeth to engage the pawls 174 and the engagement pawls 178. According to one embodiment, the mode selector 162 and the actuator 158 have demarcations corresponding to the various spacings of the ratchet teeth.

According to one embodiment, the plunger 194 also has a flat side 204 so that the user can rotate the plunger 194 to an orientation in which the ratchet teeth 168 are disengaged from the pawls 174 and the engagement pawls 178, and the flat side 204 is aligned with the pawls 174 and the engagement pawls 178. Thus, the plunger 194 can also be employed to reconstitute a lyophilized medicament.

In addition, although the plunger 194 is illustrated as having two sides with respective pluralities of spaced-apart ratchet teeth, one skilled in the art will appreciate that the plunger 194 may have 3, 4, 5, 6, 7, 8, 9, 10, or more sides with respective pluralities of differently-spaced-apart ratchet teeth to provide a greater selection for a user without departing from the scope of the present invention. Additionally, although the pawls 174 and the engagement pawls 178 are illustrated as being opposing pairs, a single pawl 174 and a single engagement pawl 178 may be employed to accommodate a greater number of sides with differently spaced ratchet teeth on the plunger 194 without departing from the scope of the present invention.

Although only a few embodiments of the present invention have been shown and described, the present invention is not limited to the described embodiments. Instead, it will be appreciated by those skilled in the art that changes may be made to these embodiments without departing from the principles and spirit of the invention, the scope of which is defined by the claims and their equivalents.

What is claimed is:

1. A medical injector, comprising:
a body having a distal end and a proximal end;
a displaceable plunger disposed in the body, the plunger having a plurality of spaced-apart ratchet teeth disposed along the length thereof;
at least one indexer formed to engage the plunger, wherein the indexer is configured to allow the plunger to displace distally toward the distal end of the body but not proximally toward the proximal end of the body;
an actuator having an engagement portion formed to engage one or more of the ratchet teeth, wherein the actuator is displaceable to a ready state, the engagement portion being displaced proximally relative to the plunger upon the actuator being displaced to the ready state, the indexer preventing proximal movement of the plunger thereby allowing the engagement portion to bypass one or more of the ratchet teeth upon the actuator being displaced to the ready state, and wherein the actuator is displaceable from the ready state to cause actuation of the medical injector, the displacement from the ready state causing distal displacement of the engagement portion with the engagement portion engaging one or more of the ratchet teeth and causing distal displacement of the plunger; and
a rotary knob rotatably disposed at a proximal end of the body;
wherein one of the actuator and an interior of the body comprises an axial groove and the remaining one of the actuator and the interior of the body comprises a corresponding axial key slidably received in the axial groove to guide axial displacement of the actuator relative to the body and prevent rotation of the actuator relative to the body;
wherein one of the actuator and the rotary knob comprises a groove with a substantially helical portion and the remaining one of the actuator and the rotary knob comprises a corresponding key slidably received in the groove; and
wherein rotation of the rotary knob induces displacement of the key relative to the groove, thereby axially displacing the actuator relative to the body.

2. The medical injector according to claim 1, wherein the actuator is slidably displaceable relative to the body.

3. The medical injector according to claim 1, further comprising a rocker for determining force transmission from the actuator to the plunger and/or for defining a dosage amount, the rocker being pivotably connected to the actuator and pivotably connected to the body.

4. The medical injector according to claim 1, wherein a plurality of dose indicating holes are formed in the body, and wherein a pointer extends from the actuator, the pointer being configured to be visible through a single one of the dose indicating holes at an instance, the pointer providing an indication of the remaining number of doses in the medical injector.

5. The medical injector according to claim 1, further comprising a limiter rib disposed on the plunger to correspond with a last amount of available medicament, wherein the limiter rib is configured to interferingly engage a portion of the actuator and block proximal movement of the actuator therepast.

6. A medical injector, comprising:
a body having a distal end and a proximal end;
a plunger displaceably disposed in the body, the plunger having a plurality of spaced-apart ratchet teeth disposed along the length thereof, the plunger selectively displacing a stopper to dispense a medicament from said medical injector;
an indexer disposed within the body to engage the plunger to permit distal displacement of the plunger and substantially prevent proximal displacement of the plunger;
an actuator having an engagement portion to engage the plunger to permit proximal displacement of the actuator relative to the plunger and substantially prevent distal displacement of the actuator relative to the plunger; and
a rotary knob rotatably disposed at a proximal end of the body;

wherein one of the actuator and an interior of the body comprises an axial groove and the remaining one of the actuator and the interior of the body comprises a corresponding axial key slidably received in the axial groove to guide axial displacement of the actuator relative to the body and prevent rotation of the actuator relative to the body;

wherein one of the actuator and the rotary knob comprises a groove with a substantially helical portion and the remaining one of the actuator and the rotary knob comprises a corresponding key slidably received in the groove;

wherein rotation of the rotary knob induces displacement of the key relative to the groove, thereby axially displacing the actuator relative to the body;

wherein upon proximal displacement of the actuator relative to the body to a ready state, one or more of the ratchet teeth bypass the engagement portion to proximally displace the actuator relative to the plunger; and wherein upon distal displacement of the actuator relative to the body from the ready state, the actuator engages one or more of the ratchet teeth to distally displace the plunger relative to the indexer to distally displace the stopper to dispense medicament from the medical injector.

7. The medical injector according to claim 6, further comprising a rocker for determining force transmission from the actuator to the plunger and/or for defining a dosage amount, the rocker being pivotably connected to the actuator and pivotably connected to the body.

8. The medical injector according to claim 6, wherein at least one key is formed to extend from one of the actuator and the body, and a channel is formed in the remaining one of the actuator and the body, the key being configured to be slidably received in the channel for defining a dosage amount.

9. The medical injector according to claim 6, further comprising a limiter rib disposed on the plunger to correspond with a last amount of available medicament, wherein the limiter rib is configured to interferingly engage a portion of the actuator and block proximal movement of the actuator therepast.

10. The medical injector according to claim 6, wherein a plurality of dose indicating holes are formed in the body, and wherein a pointer extends from the actuator, the pointer being configured to be visible through a single one of the dose indicating holes at an instance, the pointer providing an indication of the remaining number of doses in the medical injector.

* * * * *